United States Patent
Park et al.

(10) Patent No.: US 10,195,246 B2
(45) Date of Patent: Feb. 5, 2019

(54) USE OF CPNE7 FOR DIFFERENTIATING NON-DENTAL MESENCHYMAL STEM CELLS INTO ODONTOBLASTS, REGENERATING DENTAL PULP AND TREATING DENTIN HYPERSENSITIVITY

(71) Applicant: SEOUL NATIONAL UNIVERSITY R&DB FOUNDATION, Seoul (KR)

(72) Inventors: Joo-Cheol Park, Seoul (KR); Han-Wool Choung, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 42 days.

(21) Appl. No.: 15/381,984

(22) Filed: Dec. 16, 2016

(65) Prior Publication Data

US 2017/0100458 A1  Apr. 13, 2017

Related U.S. Application Data

(63) Continuation-in-part of application No. PCT/KR2015/004085, filed on Apr. 24, 2015.

(30) Foreign Application Priority Data

Jun. 19, 2014  (KR) ........................ 10-2014-0075037

(51) Int. Cl.
| | | |
|---|---|---|
| *A61K 38/17* | (2006.01) | |
| *A61K 33/06* | (2006.01) | |
| *A61K 33/24* | (2006.01) | |
| *A61K 33/26* | (2006.01) | |
| *A61K 6/06* | (2006.01) | |
| *A61K 6/08* | (2006.01) | |
| *C12N 5/0775* | (2010.01) | |
| *A61K 35/12* | (2015.01) | |
| *C07K 14/47* | (2006.01) | |
| *C12N 15/113* | (2010.01) | |

(52) U.S. Cl.
CPC ........ *A61K 38/1709* (2013.01); *A61K 6/0612* (2013.01); *A61K 6/0662* (2013.01); *A61K 6/0675* (2013.01); *A61K 6/08* (2013.01); *A61K 33/06* (2013.01); *A61K 33/245* (2013.01); *A61K 33/26* (2013.01); *A61K 35/12* (2013.01); *C07K 14/4702* (2013.01); *C12N 5/0664* (2013.01); *C12N 15/113* (2013.01); *C12N 15/1138* (2013.01); *C12N 2310/14* (2013.01); *C12N 2501/998* (2013.01); *C12N 2506/1392* (2013.01)

(58) Field of Classification Search
None
See application file for complete search history.

(56) References Cited

PUBLICATIONS

Choung, et al. (May 15, 2013 online) "The role of preameloblast-conditioned medium in dental pulp regeneration", Journal of Molecular Histology, 44: 715-21.*
Choung, et al. (2016): "Tertiary Dentin Formation after Indirect Pulp Capping Using Protein CPNE7", Journal of Dental Research, 95 (8): 906-12.*
Sawicki, et al. (2008) "Histological evaluation of mineral trioxide aggregate and calcium hydroxide in direct pulp capping of human immature permanent teeth", American Journal of Dentistry, 21(4): 262-6 (Abstract Only).*
Li, et al. (Epub May 13, 2013) "Differentiation of Mesenchymal Stem Cells from Human Umbilical Cord Tissue into Odontoblast-Like Cells Using the Conditioned Medium of Tooth Germ Cells In Vitro", vol. 2013, Article ID 218543, 10 pages.*
Petrou et al., "A randomized clinical trial on the use of medical Portland cement, MTA and calcium hydroxide in indirect pulp treatment", Clin Oral Invest (2014) 18:1383-1389.

* cited by examiner

*Primary Examiner* — Robert M Kelly
(74) *Attorney, Agent, or Firm* — Vorys, Sater, Seymour & Pease LLP; Mih Suhn Koh

(57) ABSTRACT

The present invention relates to: composition for differentiating non-dental mesenchymal stem cells into odontoblasts comprising CPNE7 protein or gene; method for differentiating in vitro non-dental mesenchymal stem cells using the same; and also use thereof.

12 Claims, 29 Drawing Sheets
Specification includes a Sequence Listing.

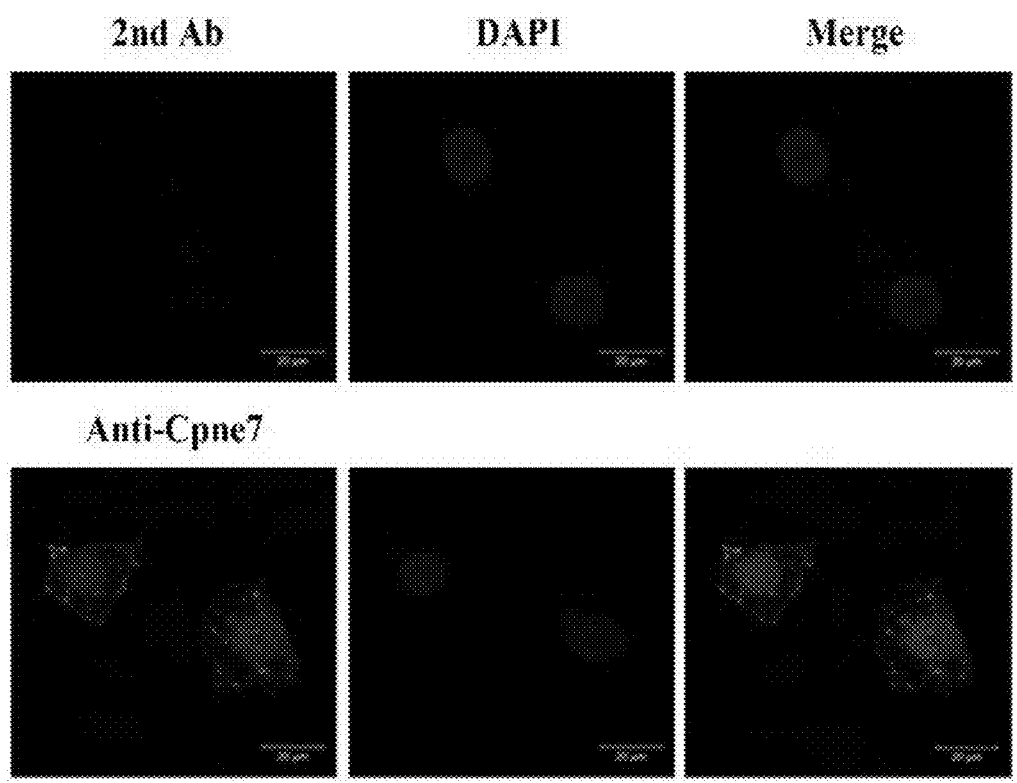

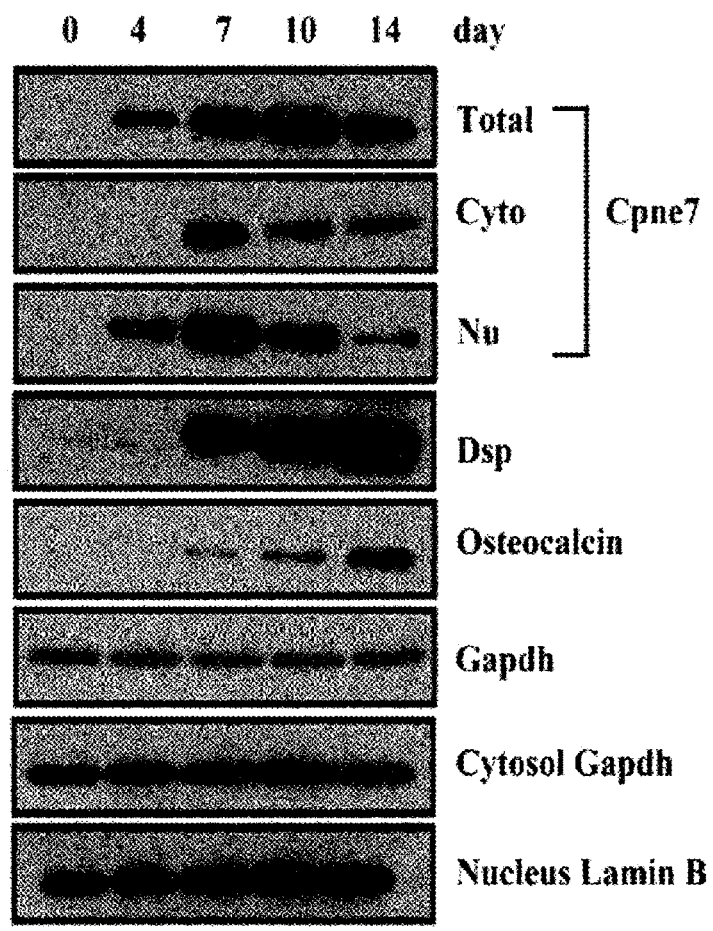

FIG. 6
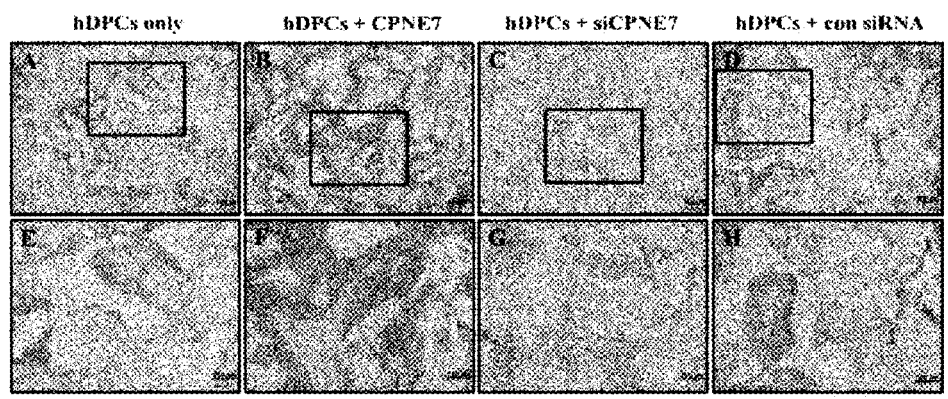
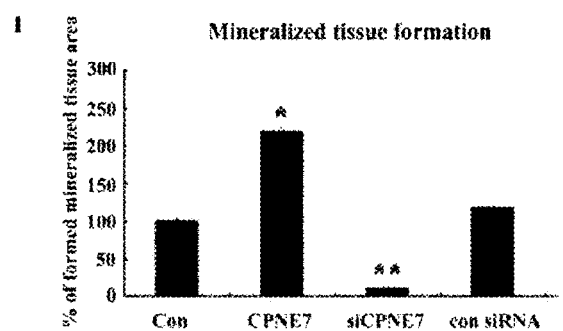

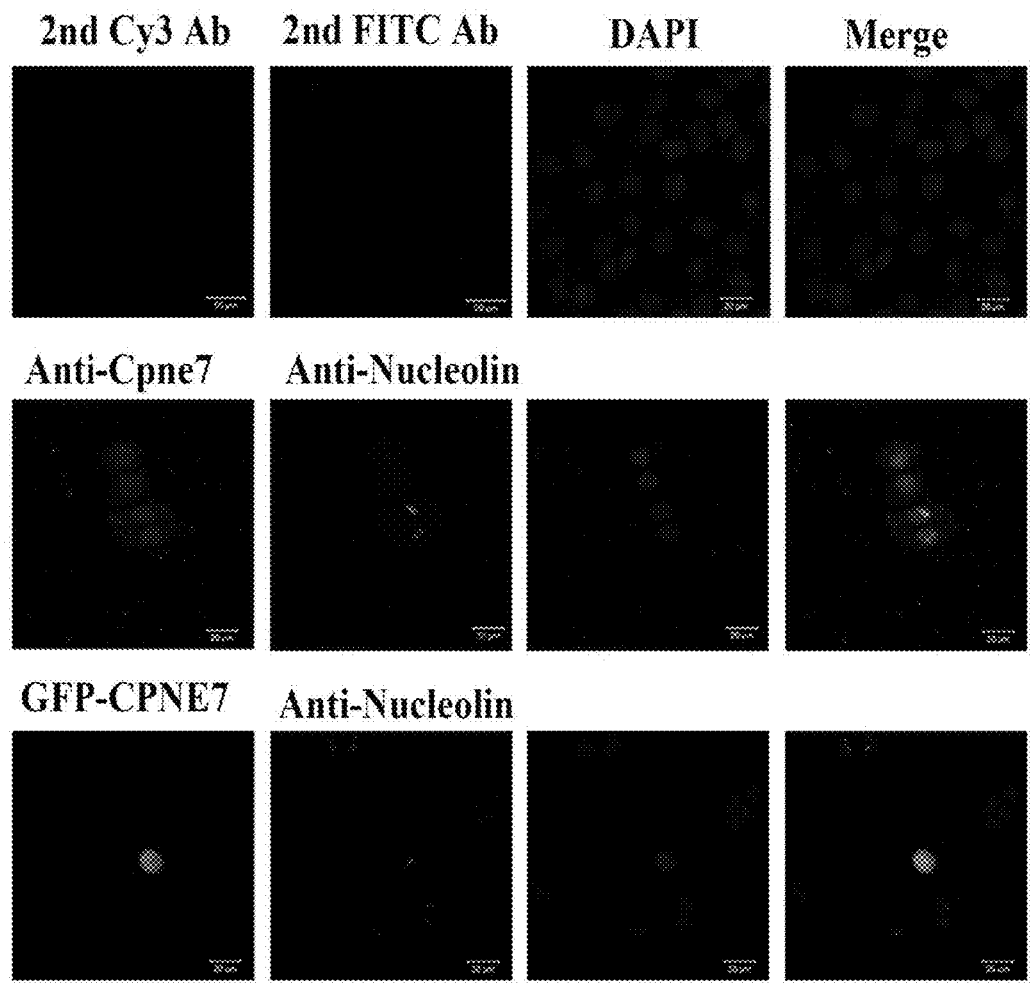

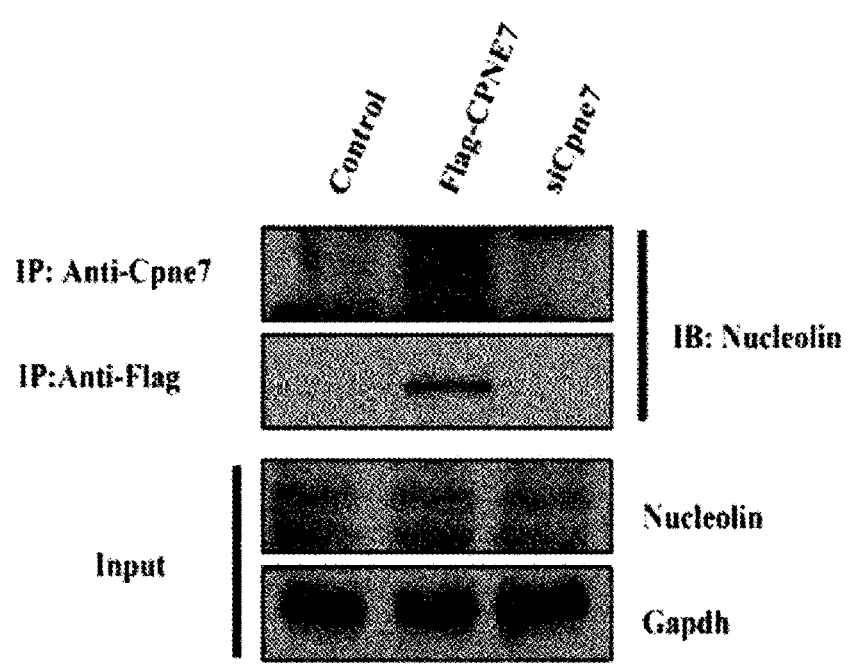

FIG. 9C
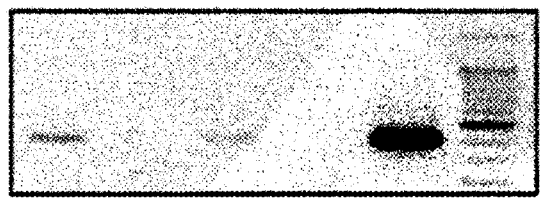
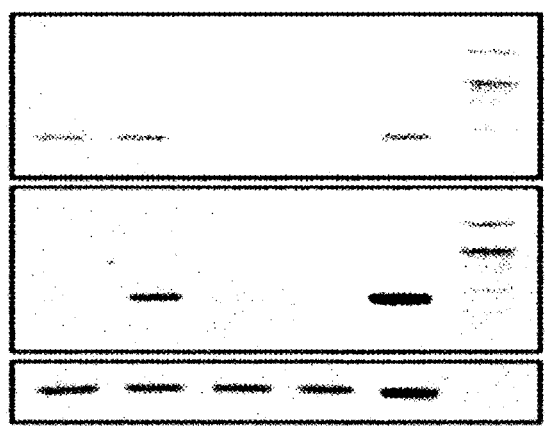

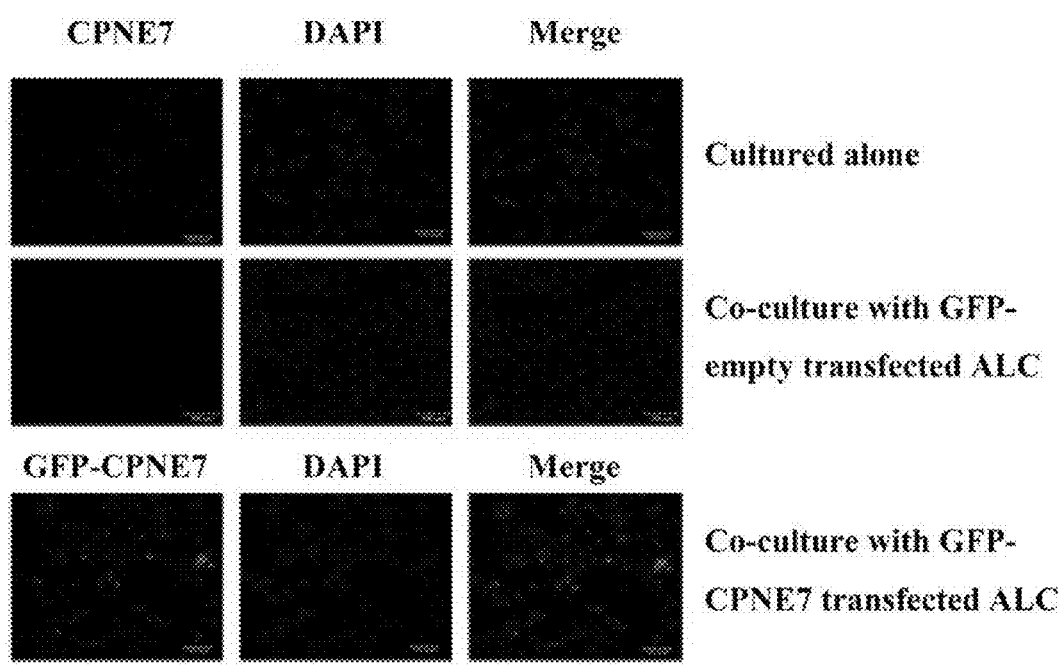

FIG. 11
MDPC-23
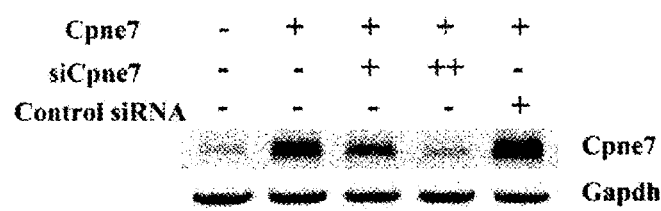
HEK293
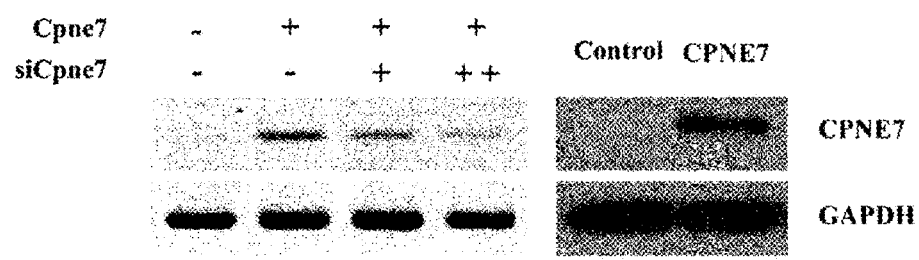

MDPC-23

FIG. 13
MDPC-23

Mutant Sequences

Control   siNucleolin   Control   siNucleolin

Nucleolin

AP-1 binding site (-199) in DSPP promoter

SEQ ID NO: 15  WT: Biotin-ATAGGCACACTGACTCTTTAAACCC
SEQ ID NO: 16  MT: Biotin-ATAGGCACACTTACCCTTTAAACCC Nucleolin AP-1 binding site (-307) in DSPP promoter SEQ ID NO: 17  WT: Biotin-AATGCAGGGTGACAGAGTCTAAGTG
SEQ ID NO: 18  MT: Biotin-AATGCAGGGTGCCCGAGTCTAAGTG

USE OF CPNE7 FOR DIFFERENTIATING NON-DENTAL MESENCHYMAL STEM CELLS INTO ODONTOBLASTS, REGENERATING DENTAL PULP AND TREATING DENTIN HYPERSENSITIVITY

STATEMENT OF GOVERNMENT SUPPORT

The invention was made with government support under grant number 2016R1A2B3006584 "Control of odontoblast differentiation and dentin formation" awarded by the National Research Foundation, Republic of Korea.

CROSS-REFERENCE TO RELATED APPLICATIONS

The present application is a national stage application of International Patent Application No. PCT/KR2015/004085, filed Apr. 24, 2015, and claims the benefit of Korean Patent Application No. 2014-0075037, filed Jun. 19, 2014 in the Korean Intellectual Property Office, the disclosure of which are incorporated herein.

STATEMENT OF SEQUENCE LISTING

The Sequence Listing submitted in text format filed on Dec. 15, 2016, named "SequenceListing.txt", created on Dec. 5, 2015 (4.68 KB), is incorporated herein by reference.

BACKGROUND

Field of the Invention

The present disclosure generally relates to composition and method for differentiating non-dental mesenchymal stem cells into odontoblasts comprising CPNE7 and pharmaceutical composition for regenerating dental pulp and treating dentin hypersensitivity using the same Description of the Related Art Dental pulp is a soft and non-calcified tissue at the center of the tooth occupying the pulp chamber containing nerves and blood vessels. Dentin protects the underlying dental pulp against various harmful stimuli. If there is partial loss of the overlying dentin in response to mechanical trauma, such as tooth preparation, removal of dentinal decay, or tooth attrition, dentinal tubules and odontoblast processes will be exposed to the external environment, causing pulp disease such as dentin hypersensitivity, pulpitis and apical periodontitis and the like. Pulpitis caused by bacterial infection may lead to severe pulp diseases and may successively progress to pulp hyperemia, pulpitis and pulp necrosis. Pulp necrosis prevents the blood supply to the pulp leading to the apical periodontitis or damage to the entire tooth.

For treatment of the apical periodontitis or pulp diseases, pulp capping material and pulp canal filling materials are used and include calcium hydroxides, MTA (Mineral Trioxide Aggregate), Gutta-percha and the like. MTA shows an excellent leakage sealing ability and good biocompatibility with dental tissues.

However the use of MTA is hampered by its high cost and discoloration leading to an esthetic problem. Gutta-percha is relatively low cost and has good flow characteristics. However it is not a physiologically acceptable method because it has disadvantages of causing chronic infectious reactions, low adhesiveness to the dentin, and low ability to regenerate the damaged tissues particularly leading to a loss of viability of the pulp. Up to now, conservative treatments for pulp and dentin diseases present problems of resulting in the weak or brittle teeth or reinfection. Several IPC (Indirect Pulp Capping) studies have shown varying success rates of 73%-97%, but the question of which capping material is optimal is still debatable (Petrou et al. A randomized clinical trial on the use of medical Portland cement, MTA and calcium hydroxide in indirect pulp treatment. Clin Oral Investig. 18(5):1383-1389 2014).

Korean Patent Application Publication No. 2012-0089547 discloses compositions for regenerating dentin or pulp tissues, or forming hard tissues containing ameloblast apical bud cells, or cultures thereof. Korean Patent Application Publication No. 2009-0033643 discloses tooth stem cells derived from tooth follicles having excellent colony-forming activity and reproductive capability, and a method for cultivating the same.

None are disclosed in the prior arts regarding using dental or nondental mesenchymal stem cells for regeneration of dentin or pulp tissues, or for treating pulp diseases by differentiating the above cells to odontoblasts.

SUMMARY OF THE INVENTION

One aspect of the present disclosure provides a method of treating dentin hypersensitivity by administering to a subject in need thereof an effective amount of (i) an isolated CPNE7 protein or a gene encoding the same; (ii) a cell overexpressing a CPNE7 protein; (iii) an odontoblast differentiated from (iii); or (iv) (i) in combination with a mesenchymal stem cell.

Other aspect of the present disclosure provides method of differentiating non-dental mesenchymal stem cell expressing a Nucleolin and a Dspp into odontoblasts by treating the mesenchymal stem cell with a CPNE7 protein or a gene encoding the same, wherein the CPNE7 protein interacts with the Nucleolin so as to regulate an expression of the Dspp. One feature of the present composition includes that the differentiation is induced by an interaction between the CPNE7 and Nucleolin so as to regulate an expression of Dspp.

Still other aspect of the present disclosure provides a method of generating reactionary pulp in an affected area by treating the area with an effective amount (i) an isolated CPNE7 protein or a gene encoding the same; (ii) a cell overexpressing a CPNE7 protein; (iii) an odontoblast differentiated from (iii); or (iv) (i) in combination with a mesenchymal stem cell.

Still other aspect of the present disclosure provides a method of regenerating a dentin or a pulp by treating the affected area with an effective amount (i) an isolated CPNE7 protein or a gene encoding the same; (ii) a cell overexpressing a CPNE7 protein; (iii) an odontoblast differentiated from (iii); or (iv) (i) in combination with a mesenchymal stem cell.

Still other aspect of the present disclosure provides a method of indirect pulp capping by treating the affected area with an effective amount (i) an isolated CPNE7 protein or a gene encoding the same; (ii) a cell overexpressing a CPNE7 protein; (iii) an odontoblast differentiated from (iii); or (iv) (i) in combination with a mesenchymal stem cell.

In the foregoing methods, the cell overexpressing a CPNE7 protein is a mesenchymal stem cell.

In the foregoing methods, the mesenchymal stem cell is of non-dental origin.

In the foregoing methods, material for indirect capping such as MTA or calcium hydroxide ($CaOH_2$) can be advantageously used to the effect as described herein in combination with at least one of (i), (ii), (iii), and (iv).

Still other aspect of the invention provides a composition comprising an isolated CPNE7 protein or a gene encoding the same and MTA or calcium hydroxide ($CaOH_2$).

Still other aspect of the invention provides a composition comprising CPNE7 protein or gene encoding the same for differentiating non-dental mesenchymal cell to odontoblast.

In the foregoing methods and compositions, the non-dental mesenchymal stem cell includes a bone marrow mesenchymal stem cell or an adipose stem cell.

Still in the foregoing methods and composition, the non-dental mesenchymal stem cell is autologous, allogenic, or xenogenic origin.

Still in other aspect, there is also provided a cell therapeutic agent or cell therapeutics comprising a mesenchymal stem cell overexpressing CPNE7, a precursor cell therefrom which can be differentiated into odontoblast, or a odontoblast differentiated therefrom as an effective ingredient for regeneration of dentin or pulp tissue.

In the foregoing cell therapeutic agent, the agents are used for treating dentin hypersensitivity, pulp hyperemia, pulpits, pulp degeneration, pulp necrosis, or gangrenous pulp.

Still in the foregoing cell therapeutic agent, the agent may be administered to an exposed pulp, an empty pulp cavity with pulp legion being removed.

Still in other aspect, there is also provided a composition comprising CPNE7 or gene encoding the same for regenerating dentin or pulp tissue via inducing or stimulating the differentiation of non-dental mesenchymal stem cells into odontoblast.

Still in other aspect, there is also provided a use of CPNE7 or gene encoding the same for differentiating non-dental mesenchymal stem cells into odontoblast.

Still in other aspect, there is also provided a use of CPNE7 or gene encoding the same for regenerating dentin or pulp tissue.

The foregoing summary is illustrative only and is not intended to be in any way limiting. Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 1A to 1C show the expression of CPNE7 during the differentiation of ameloblast, in which ALCs (ameloblast lineage cell) were incubated for at least 2 weeks in the differentiation medium. FIG. 1A is a result of RT-PCR to analyze the mRNA expression of CPNE7, Odam, and Mmp-20, in which GAPDH was used as a loading control. FIG. 1B is a western blot result of a CPNE7, Odam, and Mmp-20 expression in ALCs analyzed using the whole cell extract on the indicated days. FIG. 1C is a result of immunofluorescence assay to localize CPNE7 in cells, in which a secondary antibody alone was used as a negative control and cells were counter-stained with DAPI. Scale bare indicates 20 μm.

FIG. 2A is a result of immunohistochemistry assay to examine the expression during the tooth development in mice performed on embryonic day 19 (E19) and postnatal days 7 (P7) and 10 (P10). It was found that CPNE7 proteins are localized in inner enamel epithelium and stratum intermedium at E19; in differentiating odontoblasts at P7; and in dentin, predentin and differentiated odontoblasts at P10 (indicated as arrows). IEE: inner enamel epithelium, SI: stratum intermedium, Od: odontoblast, Am: ameloblasts, E: enamel, D: dentin. Scale Bar: 200 μm. FIG. 2B is a schematic diagram of co-culture system. ALCs were seeded in the upper chamber with CPNE7 tagged with flag, and odontoblast MDPC-23 cells were seeded in the bottom chamber. Epi: Epithelial cells, Mes: Mesenchymal stem cells. In the co-culture system, the translocation of CPNE7 protein tagged with flag synthesized in ALC to MDPC-23 cells were detected by western blot. GAPDH was used as a loading control.

FIGS. 3A to 3C show the expression of CPNE7 during the differentiation of odontoblasts. Odontoblast cell line MDPC-23 cells were cultured in the differentiation medium for at least 2 weeks. FIG. 3A is a result of immunofluorescence assay to determine the location of CPNE7 in MDPC-23 cells in which a secondary antibody alone was used as a negative control. The cells were counter-stained with DAPI. Scale Bar: 20 μm. FIG. 3B is a result of quantitative RT-PCR to measure the mRNA level of CPNE7, Dspp, and Osteocalcin at the days indicated. The values were represented as mean±SD from three independent experiments. *$P<0.01$ compared to the control. FIG. 3C is a western blot result of MDPC-23 to detect CPNE7, Dspp, and Osteocalcin at the indicated days, in which GAPDH was used as a loading control. Cytosol GAPDH and nucleus lamin B was used as a control for cellular fraction. Total: whole cell extract, Cyto: cytosol fraction, Nu: nucleus fraction.

FIG. 4A shows a result of real time PCR analysis of Dspp mRNA expression. FIG. 4B show a result of western blot analysis of CPNE7 and Dspp expression. GAPDH was used as a loading control. In FIGS. 4C and 4D, MDPC-23 cells were treated with 100 ng/ml rCPNE7. FIG. 4C is a result of real time PCR analysis of CPNE7 and Dspp mRNA. FIG. 4D is a result of western blot analysis of CPNE7 and Dspp expression. FIG. 4E is a result of western blot analysis of CPNE7 and Dspp expression in MDPC-23 cells from the co-culture system. FIG. 4F is a result of western blot analysis of Dspp expression in MDPC-23 cells after the inactivation of CPNE7 in CM. The transcriptional activity from Dspp promoter in the presence of CPNE7 or CPNE7 siRNA in MDPC-23 cells was measured using luciferase assay. FIG. 4F is a result showing that the transcriptional activity of Dspp was activated by the overexpression of CPNE7, which, however, was prevented by a knock-down of CPNE7 using siRNA. All the values were represented as mean±SD from three independent experiments. *$P<0.05$, **$P<0.01$ compared to the controls.

FIG. 6 shows the histomorphological analysis results of mineralized tissue formation in hDPCs where CPNE7 proteins were overexpressed or inactivated, in which hDPCs were not transfected (A and E), or were transfected with CPNE7 for overexpression (B and F), CPNE7 siRNA (C and G), control siRNA (D and H) construct. Then the cells were subcutaneously transplanted to immune compromised mice. The regenerated tissues were H&E stained (E-H). The boxed areas in A-D were enlarged. Scale bar: 200 µm. The total area of the mineralized tissue generated from four groups was analyzed using LS starter program. All the values were represented as mean±SD from three independent experiments. *P<0.05, **P<0.01 compared to the controls.

FIGS. 9A to 9D show the regulation of Dspp by the complex of CPNE7 and Nucleolin. FIG. 9A shows the co-localization of CPNE7 and Nucleolin in MDPC-23 cells detected by immune-fluorescence, in which secondary antibody conjugated to Cy3 (2nd Cy3) and FITC (2nd FITC) was used as a negative control. The cells were counterstained with DAPI. Scale Bar: 20 µm. FIG. 9B is a western blot analysis result in which MDPC-23 cells were transfected with flag-tagged CPNE7 expression or CPNE7 siRNA construct, immunoprecipitated (IP) CPNE7 and whole cell extract (Input) were analyzed by western blot (IB) using anti-nucleolin antibody. FIG. 9C is a result of immunoprecipitation with preimmune serum (IgG) or Nfic-specific antibody (Upper), in which cross-linked, sheared chromatins were prepared from MDPC-23 cells transfected with CPNE7 overexpression or Nucleolin siRNA construct. ChIP assays were performed using anti-Nucleolin, anti-CPNE7, or IgG antibodies. Chromatin samples were subjected to PCR analysis using primer pairs spanning the AP-1 site on the Dspp promoter. Input: the PCR product of chromatin obtained before immunoprecipitation, IgG: preimmune serum, pos1: ChIP positive (anti-Nfic), neg: PCR negative, pos2: PCR positive, con: control, siNu: Nucleolin siRNA. FIG. 9D is a result of luciferase assay in which MDPC-23 cells were co-transfected with the indicated vectors and the transcriptional activity of the Dspp promoter was evaluated by luciferase assay. Expression levels of CPNE7, Nucleolin, and Dspp in MDPC-23 cells were evaluated by western blotting. GAPDH was used as a loading control. All values represent the mean±SD of triplicate experiments. *P<0.05, **P<0.01 compared to control.

FIG. 10 shows the translocation of CPNE7 from ALCs to MDPC-23 cells, in which ALCs transfected with GFP-tagged CPNE7 were seeded in the upper chamber, and MDPC-23 cells were seeded in the bottom chamber, and the migration of GFP-tagged CPNE7 from ALCs into MDPC-23 cells was detected by fluorescence microscopy. Cells were counterstained with DAPI. Scale bars: 100 µm.

FIG. 11 shows the regulation of the expression of CPNE7 is regulated by CPNE7 overexpression and CPNE7 siRNA in HEK293 and MDPC-23 cells, in which constructs encoding CPNE7, CPNE7 siRNA, and control siRNA were transfected into HEK293 and MDPC-23 cells (Upper); and Cpne7 expression in MDPC-23 cells was analyzed by RT-PCR (Lower) and CPNE7 expression in HEK293 cells was analyzed by RT-PCR and western blotting.

FIG. 13 shows that the Nucleolin binds to the Dspp promoter. MDPC-23 cells were transfected with Nucleolin siRNA and nuclear extracts were prepared and mixed with biotinylated Dspp promoter probes containing wild-type (WT) and mutant (MT) AP-1 sites. Nucleolin in the complex was detected by western blotting.

DETAILED DESCRIPTION OF THE EMBODIMENTS

Figure 1A:
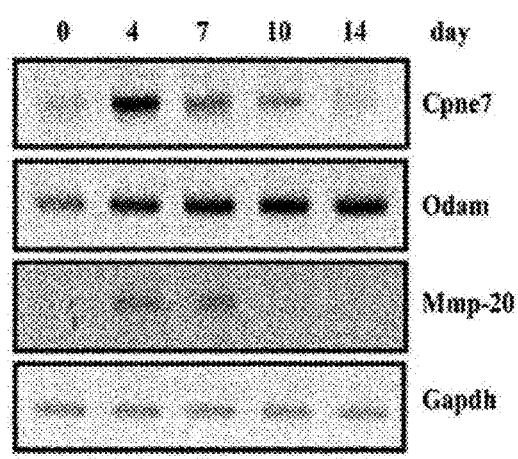
Figure 1B:
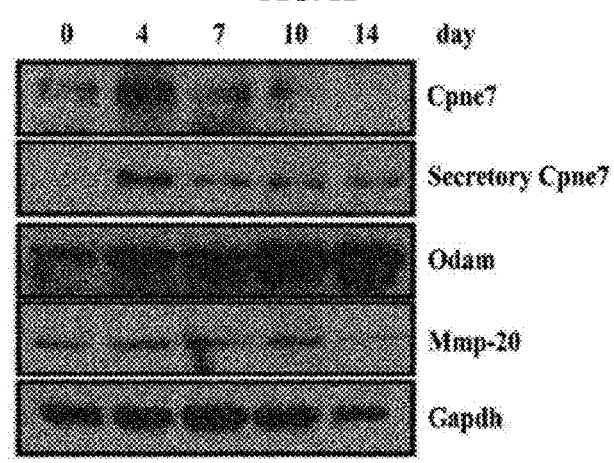
Figure 2A:
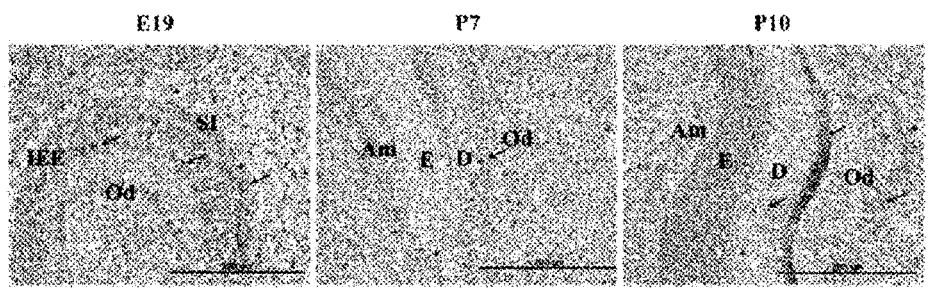
FIGS. 2A and 2B show the translocation of CPNE7 from ameloblasts to odontoblasts.
Figure 2B:
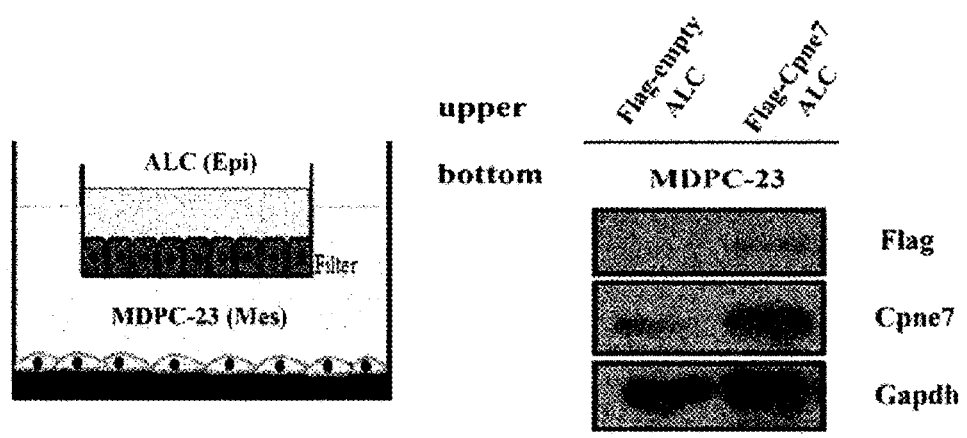

The present disclosure is based on the discovery that Cpne7 can induce the differentiation of non-dental mesenchymal stem cells into odontoblast and thus can promotes the generation of odontoblasts, which can be effectively used for treating various diseases requiring the generation of odontoblasts.

It is therefore an aspect of the present invention to provide a method and composition for differentiating non-dental mesenchymal stem cells into odontoblasts using CPNE7 protein or gene.

The term "CPNE7 protein" encoded by a gene CPNE7 refers to a member of a copine family of proteins which are a calcium dependent membrane binding protein. The protein has two C2 domains at N-terminus and von willebrand factor A domain. For the purpose of the present disclosure, various forms of CPNE7 proteins/genes of various origins may be used for the present disclosure as long as it fulfills the effects disclosed by the present disclosure. For example, included in the present disclosure are wild-type proteins or genes or fragments thereof, or mutant forms thereof in which certain bases or amino acids are artificially modified for example to improve the expression or the stability of the protein/genes, or any naturally occurring variants thereof. The modification at the genetic level may or may not be accompanied by the modification at the protein level. In the former case, the protein may comprise any one of substitution, deletion, addition and/or insertion in the amino acid sequence compared to that of wild-type. Thus also included in the present disclosure are mutants, derivatives, alleles, variants and homologues and the like. Also included in the present disclosure are degeneracy mutants in which the base modifications do not result in the corresponding changes in the amino acids.

The modification of the genes may be performed by the methods known in the art, for example, site-directed mutagenesis, Kramer et al, 1987), error prone PCR (Cadwell, R. C. and G. F. Joyce. 1992. PCR methods Appl., 2:28-33.), and point mutagenesis (Sambrook and Russel, Molecular Cloning: A Laboratory Manual, 3rd Ed. 2001, Cold Spring Harbor Laboratory Press.) and the like.

The protein which may be used in the present disclosure may be prepared by the methods known in the art, such as genetic recombination technology. For example a vector or plasmid comprising a gene encoding a protein of interest is transfected to prokaryotic or eukaryotic cells such as insect or mammalian cells of interest for expression. Then the expressed proteins are purified as needed. For example, the plasmid which may be employed is an expression vector such as pET28b (Novagen) into which a gene of interest is cloned and transferred to a cell of interest for protein expression. The proteins are isolated from the cells and then purified for further use. The proteins may be purified by precipitation, dialysis, and column chromatography, the example of which includes ion exchange chromatography, gel-permeation chromatography, HPLC (high performance liquid chromatography), reverse phase HPLC, preparative SDS-PAGE, affinity column chromatography. The affinity column chromatography may be prepared using antibody against a protein of interest.

In one embodiment, CPNE7 protein and gene are originated from a mammal such as apes and human beings, particularly from human beings. Full-length of CPNE7 as well as fragments thereof may be used for the present disclosure as long as it fulfills the present effect. By way of example, the full-length sequences which may be used for the present disclosure are GenBank ID NO. NM170684 (amino acids sequence), NP733785 (nucleic acid sequence) for mice, NM014427 (amino acids sequence), NP055242 (nucleic acid sequence) for human beings, but the sequences are not limited thereto.

In other embodiment, the genes may be provided as a vector in which the gene of interest is operatively linked to a promoter for its expression into a protein in the cells employed or used in the present methods and composition.

In the present disclosure, CPNE7 protein or gene induces the differentiation of non-dental mesenchymal stem cells into odontoblasts. Human dental pulp stem cells (hDPSC) which may be isolated from wisdom teeth have a capacity to differentiate into odontoblasts and osteoblasts. In comparison, the method using and composition comprising CPNE7 of the present disclosure is advantageous in that they can differentiate non-dental stem cells, which may be more easily obtained than the cells of dental origin, into odontoblasts and osteoblasts. Up until now, researches related the regeneration of pulp-dentin and the induction of differentiation into odontoblasts have been based on the stem cells of dental origin, which are already exposed to an induction signal for the differentiation by interacting with dental epithelial cells. Thus, the use of non-dental mesenchymal stem cells according to the present disclosure makes more cells available for the regeneration of pulp-dentin and the differentiation into odontoblasts, including dental as well as non-dental cells. Thus the present disclosure provides great advantage and conveniences in clinical applications. Also the findings of the present disclosure that the non-dental cells can be induced to differentiate into odontoblasts may provide a key to understand the fundamental mechanisms underlying the differentiation of mesenchymal stem cells into dental odontoblasts.

The odontoblasts are in contact with dentin and functions in dentinogenesis, i.e., the formation of dentin which is the substance beneath the tooth enamel on the crown. The odontoblasts are of neural crest origin that forms the part of the outer surface of the dental pulp (Victor, E.; Arana-Chavez, V. E.; Massa, L F. Odontoblasts: the cells forming and maintaining dentine. The International Journal of Biochemistry & Cell Biology, 2004 36: 136773).

The term mesenchymal stem cells of dental origin refer to stem cells that have had an interaction with and affected by the dental epithelial cells, and are of mesodermal origin. They are present in the pulp and periodontium and include 5 types: dental pulp stem cell (DPSC), stem cell from exfoliated deciduous teeth (SHED), periodontal ligament stem cells (PDLSC), stem cell from the apical papilla (SCAP), and dental follicle precursor cells (DFPC).

The non-dental mesenchymal stem cells or mesenchymal stem cells of non-dental origin of the present disclosure include stem cells which are not dental origin and not affected by the dental epithelial cells. By way of example, in the present disclosure, mesenchymal stem cells are not originated from the pulp and periodontium and include cells from cord blood, bone marrow, blood, dermis or periosteum, which are pluripotent or multipotent having a capacity to differentiate into various cell types such as adipose cells, chondrocytes, or bone cells and the like. Also, the mesenchymal stem cells have an advantage of being engrafted to the site of implant without the use of immunosuppressing agents.

In one embodiment, the mesenchymal stem cells which may be employed for the present disclosure include cells from animals, particularly mammals, more particularly human beings. Also, the mesenchymal stem cells may be originated from various tissues or organs, such as bone marrow, adipose tissue, peripheral blood or liver. In one embodiment, mesenchymal stem cells of bone marrow origin or adipose stem cells may be used. The cells employed in the present disclosure may be autologous, allogenic, or xenogenic, and particularly allogenic.

The methods of isolating and purifying mesenchymal stem cells are known in the art and they are present in small quantity in tissues such as bone marrow. For example, the cells may be isolated in reference to U.S. Pat. No. 5,486,359. Also the mesenchymal stem cells may also be separated from hematopoietic stem cells from bone marrow according to their adherence and be proliferated without the loss of differentiating ability by using the methods known in the art.

By way of example, the mesenchymal stem cells may be obtained by employing the following steps: (1) a step of isolating mesenchymal stem cells of mammals including mice or human beings, particularly human beings, from tissue or organs such as blood or bone marrow (the bone marrow may be obtained from a tibia, a femur, a spinal cord, or an ilium); (2) a step of culturing the isolated cells in a suitable medium; and a step of removing floating cells and sub-culturing to obtain the mesenchymal stem cells to be employed for the present disclosure.

The medium which may be used for the culture during the process described above includes any medium suitable for culturing the mesenchymal stem cells. Particularly, the medium comprises a serum (such as bone serum, horse serum or human serum). By way of example, the medium which may be employed for the present disclosure includes RPMI series, Eagles's MEM (Eagle's minimum essential medium, Eagle, H. Science 130:432(1959)), α-MEM (Stanner, C. P. et al., Nat. New Biol. 230:52(1971)), Iscove's MEM (Iscove, N. et al., J. Exp. Med. 147:923(1978)), 199 medium (Morgan et al., Proc. Soc. Exp. Bio. Med., 73:1 (1950)), CMRL 1066, RPMI 1640 (Moore et al., J. Amer. Med. Assoc. 199:519(1967)), F12 (Ham, Proc. Natl. Acad. Sci. USA 53:288(1965)), F10 (Ham, R. G. Exp. Cell Res. 29:515(1963)), DMEM (Dulbecco's modification of Eagle's medium, Dulbecco, R. et al., Virology 8:396(1959)), a mixture of DMEM and F12 (Barnes, D. et al., Anal. Biochem. 102:255(1980)), Way-mouth's MB752/1 (Waymouth, C. J. Natl. Cancer Inst. 22:1003(1959)), McCoy's 5A (McCoy, T. A., et al., Proc. Soc. Exp. Biol. Med. 100:115(1959)) or MCDB series (Ham, R. G. et al., In Vitro 14:11(1978)) without being limited thereto. The medium may comprise additional components to support the maintenance or growth of the cells such as antimicrobial or antifungal agents (such as penicillin or streptomycin) or glutamine and the like.

The mesenchymal stem cells may be confirmed by methods known in the art such as flow cytometry. The flow cytometry analysis is generally performed using a marker(s) specifically expressed on the surface of the mesenchymal stem cells. For example, the mesenchymal stem cells may express on its surface CD44 or CD29 markers, and/or may show a positive reaction to MHC Class I molecule, which may be used for the confirmation of the mesenchymal stem cells.

In one embodiment, CPNE7 protein or gene or composition comprising the same may applied to non-dental mesenchymal stem cells to differentiate them into odontoblast-like stem cells. In this case, CPNE7 proteins may be overexpressed in appropriate cells by transfecting the cells as described hereinafter with a gene encoding CPNE7 or with a vector including the gene. Other components which may be included in the present composition may be selected without difficulty by a person with ordinary skill in the art, for example, in reference to the present Examples.

In this perspective, the present disclosure also relates to a method of differentiating non-dental mesenchymal stem cells into odontoblasts in vivo or in vitro by using CPNE7 protein or gene, or the present composition comprising the same.

Figure 8:
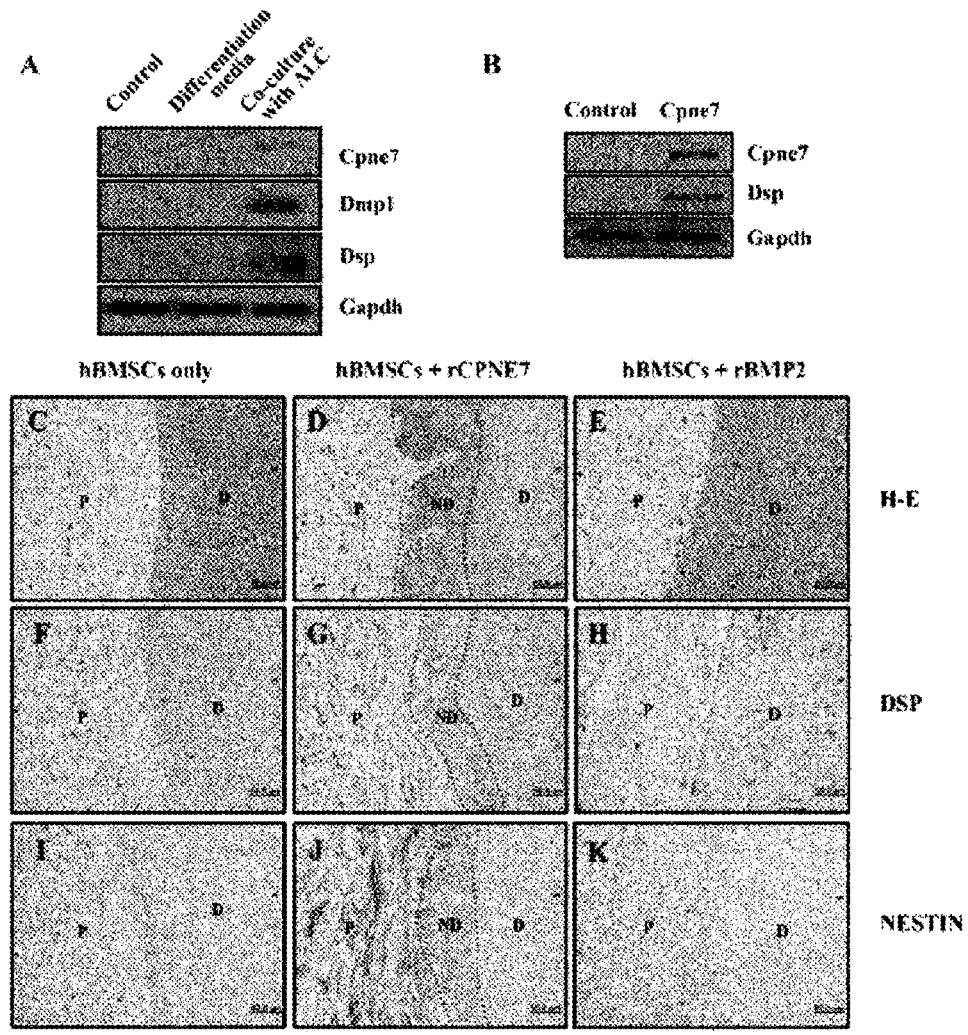
FIG. 8 shows the effect of CPNE7 on the differentiation of non-dental mesenchymal stem cell C3H10T1/2 and hBMSC in vivo and in vitro, in which the expression of CPNE7, Dmp1, and Dspp were analyzed in C3H10T1/2 cells that were cultured in the differentiation medium or co-cultured with ALC cells (A) and GAPDH was used as a loading control; C3H10T1/2 cells were transfected with CPNE7 construct for overexpression and then CPNE7 and Dspp expressions were analyzed by western blot (B); hBMSCs alone (C, F, I) or together with rCPNE7 (5 µg; D, G, J) or rBMP2 (5 µg; E, H, K) in 0.5% fibrin gel were injected into a root canal of a human tooth segment. The regenerated tissue were then stained with H-E (C-E) or immuno-stained with anti-DSP (F-H) and anti-Nestin (I-K). The dotted line in D, G and J indicates margin of the newly formed dentin including dentin tubular structure. P: the regenerated pulp, D: pre-existing dental wall, ND: newly formed physiological dentin, scale bar: 50 µm.

The odontoblasts differentiated in vitro by the present methods may be used as it is (refer to D, G and J of FIG. 8). Or the differentiated cells may be used as an active ingredient of the present composition, used in the cell therapy after being separated by methods such as flow cytometer. By way of example, various differentiated markers of odontoblasts, such as DSP, DMP1, Osteocalcin, and Nestin as a protein marker or Dspp as a genetic marker may be detected by methods known in the art to select or isolate the differentiated cells.

CPNE7 protein or gene encoding the same or the cells expressing CPNE7 or odontoblast of differentiated from MSC of non-dental origin may be applied directly onto the affected area or the area of interest to be treated, such as an exposed dentin surface, dentin cavity or exposed pulp area. Or CPNE7 protein or gene encoding the same applied may function in a way that affects the differentiation of the endogenous non-dental stem cells so as to produce the therapeutic effect by regeneration of the appropriate cells.

In this perspective, the present disclosure relates to a cell therapeutics, a cell therapy or cell therapeutic agents for regenerating pulp or dentin comprising as an effective ingredient the odontoblasts differentiated by the present methods or the composition; or the mesenchymal stem cells overexpressing CPNE7, any precursor cells derived therefrom which can be differentiated into odontoblasts or the odontoblasts differentiated therefrom. Also provided are pharmaceutical compositions comprising the cells or the cell therapeutic agent as described above for regenerating pulp or dentin. Also provided are pharmaceutical compositions comprising CPNE7 protein or gene encoding the same for regeneration of dentin or pulp.

The term cell therapeutics, cell therapy or cell therapeutic agent refers to a medicine for treatment, diagnosis or prevention of a particular disease by recovering or restoring the normal function of cells or tissues of interest using the cells of autologous, allogenic or xenogenic origin proliferated or selected or prepared in vitro, which are changed or modified to have specific biological functions or characteristics. The cell therapy or cell therapeutic agents are regulated as a medicine since 1993 in U.S.A. and 2002 in Republic of Korea. The cell therapeutic agents include stem cells to regenerate tissues or to restore the normal function of a particular organ, but are not limited thereto.

The CPNE7 protein or genes encoding the same which may be used for the present composition are as described in hereinbefore.

In one embodiment, the cells included in the cell therapeutic agents overexpress CPNE7. The cells may be prepared to overexpress a gene or protein of interest by the methods known in the art. For example, the gene encoding CPNE7 can be cloned into a eukaryotic expression vector such as vectors originated from phages, viruses or retroviruses, or plasmids in which the gene is operatively linked to a promoter. Then the expression vectors including the gene can be transfected to the cells of the present disclosure by methods known in the art. By way of example, the vectors or genes may be delivered to the cells by a calcium phosphate method, a DEAE-dextran mediated method, a positively charged lipid mediated method, an electroporation, and a transduction method using a phage system or an infection method using a virus system, but the methods are not limited thereto.

The cell therapeutic agents or the composition comprising the cells according the present disclosure may be administered via various generally known routes that are able to deliver the present cell therapeutic agents or the composition to a target site of interest. For example parenteral administration such as peritoneal, intravenous, intramuscular, subcutaneous or intradermal administrations may be used, but the routs are not limited thereto.

The therapeutic agents or compositions according to the present disclosure may be formulated as a suitable dosage form in combination with pharmaceutically acceptable carriers. The carriers or excipient which may be used for the present pharmaceutical composition include for example water, appropriate oils, saline, water based glucose and glycol and the like for parenteral formulation. Stabilizer or preservatives may also be included. Suitable stabilizers include for example antioxidants such as sodium bisulfite, sodium sulfite, or ascorbic acid and the like. Suitable preservatives include benzalconium chloride, methyl- or propyl paraben and chlorobutanol and the like. Also the present cell therapeutic agents may also include as needed according to the route of administration or the formulation, suspending agents, solubilizers, stabilizers, isotonic agents, preservatives, surfactants, diluents, excipients, pH regulating agents, buffering agents, or antioxidants and the like. Further the latest edition of Remington's Pharmaceutical Science (Mack Publishing Company, Easton Pa.) may be referred for the preparation and formulation of pharmaceutical composition.

The cell therapeutic agents of the present disclosure may be formulated as a unit dosage form in combination with acceptable carriers and/or excipients according to the methods known and easily practiced by one of ordinary skill in the art and prepared by incorporating the cell therapeutic agent into a multi-use container.

Also the present composition or cells may be administered via any appropriate device for delivery. The present cell therapy composition may comprise therapeutically effective amount of cells for treatment of disease of interest. The term "therapeutically effective amount" refers to an amount of the pharmaceutical composition or the active ingredient thereof that is able to induce biological or medical response in tissues, animals, or human beings, which can be determined by researcher, veterinarians, or medical doctors and the like, and include an amount enough to reduce or ameliorate the condition or symptom of a particular disease of interest. It is evident to the person of ordinary skill in the art that the amount varies depending on the desired effect or the types of disease or condition to be treated.

Therefore, the optimal amount of cell therapeutic agent may be determined without difficulty by one of ordinary skill in the relevant art, and adjusted depending on various factors such as types of the disease, severity of the disease, amount and types of components comprised in the composition, types of the formulation; age, sex, body weight, general condition of health and a diet of the patient; or administration time or route, secretion rate of the composition, treatment period, or other medicament administered and the like.

In one embodiment, the present cell therapeutic agent or pharmaceutical composition may be locally administered to the pathologically damaged area such as pulp hyperemia/pulpitis region due to an exposed pulp so that the pulp-dentin is generated, or empty pulp cavity after lesions in the pulp such as pulp necrosis, pulp degeneration and/or gangrenosis pulp are removed.

The cell therapeutic agent or pharmaceutical composition according to the present disclosure can be advantageously used for regeneration of dentin or pulp tissues. By regenerating the dentin or pulp, various diseases of dental pulp may be treated. The dental pulp is the part in the center of a tooth made up of soft connective tissue, cells called odontoblast, blood vessels and nerves that occupy the pulp cavity. The disease of dental pulp refers to a pathological condition in the pulp. The physical, chemical, or bacterial stimuli or irritation to the pulp initially cause pulp hyperemia due to the vasodilatation, which lead to pulpitis when the stimuli continue. Due to the anatomical characteristics that the pulp is encased by hard dentin and enamel, the infection in the pulp is likely to cause circulatory disturbance although the severity of the infection may vary depending on the strength of the stimuli or the bacterial infection. When it is left untreated, the necrosis of the pulp may occur. Dental pulp disease may be caused by various reasons and is generally due to a bacterial infection or perforation in the tooth due to dental caries, or infections through odontoclasis, cracks or periodontal pocket. Also external wound, abrasion, tooth cracks, or friction or heat from dental equipment may cause the dental pulp disease. The pulpitis due to the bacterial infection may lead to root apex and periodontal disease.

Dental pulp disease or any conditions or symptoms associated therewith described above may be treated by the present composition and cell therapeutic agents, which include for example dentin hyperesthesia, pulp hyperemia, pulpitis, pulp degeneration, pulp necrosis and gangrenous pulpitis and the like without being limited thereto.

It is important that the cell therapeutic agent according to the present disclosure is used or administered at the lowest dose level that provides a clinically significant or maximum efficacy without side effects, For example, the dose may be from $1.0 \times 10^7$ to $1.0 \times 10^8$ cells/kg (body weight), particularly from $1.0 \times 10^5$ to $1.0 \times 10^8$ cells/kg (body weight) based on the amount of odontoblast differentiated from mesenchymal stem cells. However it is evident to one of ordinary skill in the relevant art that the dose may vary considering various factors such as types of the formulation, mode of administration, age, sex, body weight, general condition of health and a diet of the patient; or administration time or route, excretion rate of the composition, degree of response to the drug, treatment period, or other medicament administered and the like. The present composition or cell therapeutic agents may be administered once or twice or more within the clinically acceptable side-effects. Or the present composition or therapeutic agents may be administered to one or two more sites. For animals other than human beings, the dosage identical to that of humans may be applied or the dosage may be adjusted after being calibrated for example in consideration of the average volume ratio of the ischemic organ between the two such as heart. The animals which may be included in the present disclosure are human beings and other mammals such as monkeys, apes, mice, rats, rabbits, sheep, cow, dogs and pigs and the like.

In this aspect, the present disclosure relates to methods of treating dentin hypersensitivity by administering to a subject in need thereof an effective amount of (i) an isolated CPNE7 protein or a gene encoding the same; (ii) a cell overexpressing a CPNE7 protein; (iii) an odontoblast differentiated from (iii); or (iv) (i) in combination with a mesenchymal stem cell.

The dentin hypersensitivity is usually developed by exposure of dentinal tubules, which are normally covered by enamel, to external environment due to various reasons such as dental caries. The dental hypersensitivity is usually treated by IPC (Indirect pulp capping) to cover the exposed dentin.

Without being bound by any theory, the present protein or gene or cells when applied to an affected area such as an exposed dentin surface for IPC moves or migrates to the pulp cavity through dentinal tubules, in which the proteins or genes stimulate or promote the differentiation of odontoblasts and the formation of dental hard tissue, thus generating reactionary dentin in the peripheral boundary of the dental pulp, and intratubular dentin in the dentinal tubules on the enamel. Thus, the transmissions of the external stimuli through the dentinal tubules are blocked, curing dentin hypersensitivity.

The present CPNE7 protein, a full or partial length, or a gene encoding the same can be used as a capping material alone or in combination with IPC material such as MTA or calcium hydroxide ($CaOH_2$). In comparison to conventional IPC materials, the present CPNE7 protein, a full or partial length, or a gene encoding the same is able to generate physiological, reactionary pulp/dentin.

Thus, in other aspect, the present disclosure relates to a method of generating reactionary pulp in an affected area by treating the area with an effective amount of (i) an isolated CPNE7 protein or a gene encoding the same; (ii) a cell overexpressing a CPNE7 protein; (iii) an odontoblast differentiated from (iii); or (iv) (i) in combination with a mesenchymal stem cell.

In still other aspect, the present disclosure relates to a method of regenerating a dentin or a pulp by treating the affected area with an effective amount of (i) an isolated CPNE7 protein or a gene encoding the same; (ii) a cell overexpressing a CPNE7 protein; (iii) an odontoblast differentiated from (iii); or (iv) (i) in combination with a mesenchymal stem cell.

In further still other aspect, the present disclosure relates to a method of indirect pulp capping by treating the affected area with an effective amount of (i) an isolated CPNE7 protein or a gene encoding the same; (ii) a cell overexpressing a CPNE7 protein; (iii) an odontoblast differentiated from (iii); or (iv) (i) in combination with a mesenchymal stem cell.

In the foregoing methods, the mesenchymal stem cell is of non-dental origin from various tissues such as adipose or bone, for example.

In the foregoing methods, the gene encoding CPNE7 may be provided as cells expressing it. In the foregoing methods, the present proteins may be overexpressed in cells by transfecting the cells with appropriate expression vectors as described herein.

Figure 15:
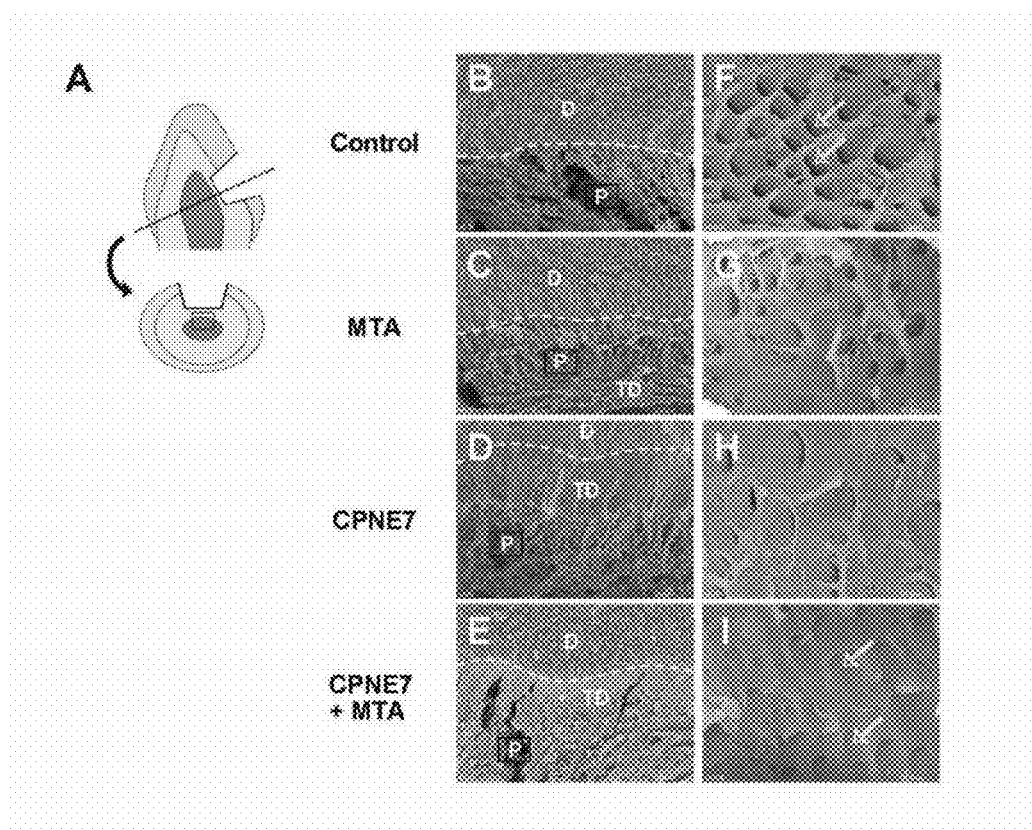
FIG. 15 shows a result of scanning electron microscopy (SEM) of pulp-side surfaces of the remaining dentin and dentinal tubules. (A) Schematic diagrams of the tissue samples for SEM analysis (2 of 6 samples from each group). (B-E) Corresponding SEM images of the dashed rectangle of A in each group. Dashed lines indicate the remaining original dentin/newly formed dentin interfaces. (F-I) Boxed areas in B-E are shown at higher magnification in F-I, which show the dentinal tubules. Arrows in F and I indicate the dentinal tubules of pulp-side dentinal surfaces. CPNE7, copine7; D, remaining dentin; MTA, mineral trioxide aggregate; P, pulp-side dentinal surface; TD, newly formed tertiary dentin. Scale bars, 100 µm (B-E) and 10 µm (F-I). indicating that CPNE7 alone or in combination with MTA can be advantageously used to treat dentin hyperesthesia.

In the foregoing methods, MTA or calcium hydroxide ($CaOH_2$) or other capping materials can be advantageously used in combination with at least one of (i), (ii), (iii), and (iv). It was found in the present disclosure that the combination therapy with CPNE7 results in the superior therapeutic effect for example, as shown in FIG. 15.

The present protein or gene, or cells may be applied to an affected area of interest, for example, to an exposed dentin surface, dentinal tubules, intentionally prepared dentin cavity or exposed pulp area, without being limited thereto.

The present protein or gene or cells when applied to an affected area such as an exposed dentin surface, and dentinal tubules are able to produce or regenerate physiological dentin, thus restoring the sensitivity and response/resistance or the dentin and pulp to external stimuli to a level normally found in healthy normal teeth.

In other aspect, the present disclosure relates to the use of CPNE7 proteins or genes encoding them for differentiation of mesenchymal stem cells to odontoblast, about which the detailed description as described above may be referred.

In still other aspect, the present disclosure relates to the use of CPNE7 proteins or genes encoding them for regeneration of the pulp tissue, about which the detailed description as described above may be referred.

The present disclosure is further explained in more detail with reference to the following examples. These examples, however, should not be interpreted as limiting the scope of the present invention in any manner.

EXAMPLES

Materials and Methods
1. Cell Culture and Co-Culture System

MDPC-23 cells were provided by Dr. J. E. Nor (University of Michigan, Ann Arbor, Mich.). ALCs were provided by Dr. T. Sugiyama (Akita University School of Medicine, Akita, Japan). C3H10T1/2 and HEK293 human embryonic kidney cells were obtained from American Type Culture Collection (ATCC, Manassas, Va.). Human BMSCs (PT-2501) were purchased from Lonza (Walkersville, Md.). MDPC-23, C3H10T1/2, hBMSCs, and HEK293 cells were cultured in Dulbecco's modified Eagle medium (DMEM; Life Technologies, Grand Island, N.Y.), and ALCs were cultured in minimum essential medium (MEM; Life Technologies) supplemented with 10% heat-inactivated fetal bovine serum (FBS; Life Technologies) and antibiotic-antimycotic (Invitrogen, Carlsbad, Calif.) at 37° C. in an atmosphere of 5% $CO_2$. To induce cell differentiation and mineralized nodule formation, confluent cells were treated with induction medium (DMEM containing 50 μg/ml ascorbic acid and 10 mM β-glycerophosphate) for up to 2 weeks.

For co-culture of ALCs with MDPC-23 cells, Transwell® permeable supports (Corning Inc., Corning, N.Y.) were used. The ALCs were seeded in the upper compartment of the transwell, and the MDPC-23 cells were seeded in the lower compartment of the dish. When cells reached 80-90% confluence, the upper compartment was combined with the lower compartment.

2. Western Blot Analysis

To prepare whole cell extracts, the cells were washed three times with PBS, scraped into 1.5-ml tubes, and pelleted by centrifugation at 12,000 rpm for 2 min at 4° C. After removal of the supernatant, the pellet was resuspended in lysis buffer (50 mM Tris-Cl, pH 7.4, 150 mM NaCl, 1% NP-40, 2 mM EDTA, pH 7.4) and incubated for 15 min on ice. Cell debris was removed by centrifugation. Thirty micrograms protein were separated by 10% sodium dodecyl sulfate-polyacrylamide gel electrophoresis (SDS-PAGE) and transferred to nitrocellulose membranes. The membranes were blocked for 1 h with 5% nonfat dry milk in PBS containing 0.1% Tween 20 (PBS-T), and incubated overnight with primary antibody diluted in PBS-T (1:1000) at 4° C.

Rabbit and affinity-purified polyclonal anti-Odam, anti-Cpne7, and anti-Dsp antibodies were produced as described previously (1, 2). The Flag (F3165) antibody was purchased from Sigma-Aldrich (St. Louis, Mo.). The Mmp-20 (sc-26926), Lamin B (sc-6216), Osteocalcin (sc-30044), Nucleolin (sc-8031), and Gapdh (sc-25778) antibodies were purchased from Santa Cruz Biotechnology. The Dmp1 antibody (ab103203) was purchased from Abcam (Cambridge, UK). After washing, the membranes were incubated with anti-mouse (sc-2031), anti-rabbit (sc-2004), or anti-goat (sc-2768) IgG secondary antibody conjugated to horseradish peroxidase (1:5000; all from Santa Cruz Biotechnology) for 1 h. The labeled protein bands were detected using an enhanced chemiluminescence system (GE Healthcare, Chalfont St. Giles, UK), and the bands were measured by densitometric analysis of the developed autoradiography films.

3. DSPP Promoter Reporter Assay

For Luciferase assay, MDPC-23 cells were seeded in 24-well culture plate at a density of $5 \times 10^4$ cells/well. After 24 hr, the cells were transiently transfected using Lipofectamine Plus™ according to the manufacturer's instruction. For transfection, constructs used were 0.5 µg of pGL3 basic (control), pGL3 DSPP promoter (−1000~+1), CPNE7 expression plasmid, CPNE7 siRNA, nucleolin siRNA, control siRNA. Then the luciferase assay was performed on the transfected cells 48 hr after the transfection.

4. ChIP Assay

After transfection with the indicated plasmid DNA using Metafectene® Pro reagent, MDPC-23 cells were crosslinked in 1% formaldehyde for 10 min at 37° C., rinsed twice with cold PBS, and swollen on ice in SDS lysis buffer (1% SDS, 10 mM EDTA, 50 mM Tris-HCl, pH 8.1) for 10 min. The nuclei were sonicated on ice. The supernatants were obtained by centrifugation for 10 min and diluted 10-fold in ChIP dilution buffer (0.01% SDS, 1.1% Triton X-100, 1.2 mM EDTA, 16.7 mM Tris-HCl, pH 8.1, and 167 mM NaCl). The fragmented chromatin mixture was incubated with anti-Nfic, anti-Nucleolin, anti-Cpne7, or IgG (1:250) on a rotator at 4° C. for 4 h. Thirty microliters of protein A/GPLUS-agarose were added and incubated at 4° C. for 1 h with rotation to collect the antibody/chromatin complexes. The precipitated chromatin complexes were recovered and dissociated according to the manufacturer's protocol (Millipore, Billerica, Mass.). The final DNA pellets were recovered and analyzed by PCR using primers that encompass the Dspp promoter region (390 bp), mouse Dspp-400 region: forward 5'-gggtcttaaatagccagtcg-3' SEQ ID NO:1 and mouse Dspp-10 region: reverse, 5'-ctgagagtggcacactgt-3' SEQ ID NO:2. PCR was carried out under conditions of 35 cycles of 94° C. for 30 s, 55° C. for 30 s, and 72° C. for 1 min. The PCR products were electrophoresed in a 1% agarose gel, stained with ethidium bromide, and visualized under ultraviolet light.

5. Immunofluorescent Staining

MDPC-23 cells were fixed in 4% paraformaldehyde at 4 for 30 min, and permeabilized in PBS containing 0.15% Triton X-100 and nonspecific bindings were removed by using 2% bovine serum. After washing, the cells were incubated with anti-Cpne7 and anti-Nucleolin antibodies for 4 h followed by the addition of anti-mouse or anti-rabbit IgG antibody conjugated to fluorescent material for 2 hrs in darkness. The nuclei were counter stained with DAPI. The cells were then washed and examined under a fluorescent microscope.

6. Fluorescence Microscopy

The cells in Nunc™ Lab-Tek™ II chambered cover glasses (Thermo Scientific, Waltham, Mass.) were washed with PBS, fixed with 4% paraformaldehyde in PBS for 10 min at room temperature, and then permeabilized for 10 min in PBS containing 0.5% Triton X-100. After washing, the cells were incubated with anti-Cpne7 (1:200) and anti-Nucleolin (1:200) antibodies in blocking buffer (PBS and 1% bovine serum albumin) for 1 h followed by the addition of a fluorescein isothiocyanate (FITC)- or Cy3-conjugated anti-mouse or anti-rabbit IgG antibody (1:200, GE Healthcare). After washing, the cells were visualized using an Olympus AX70 fluorescence microscope (Tokyo, Japan). Chromosomal DNA in the nucleus was stained with 4', 6-diamidino-2-phenylindole (DAPI; Sigma-Aldrich).

7. Co-IP Assay

After transfection with the indicated plasmid DNA using Metafectene® Pro reagent, MDPC-23 cells were washed in PBS, and the cell lysates were prepared by adding 1 ml of co-IP buffer (50 mM Tris-Cl, pH 7.5, 150 mM NaCl, 0.1% NP-40, 5 mM EDTA) supplemented with protease inhibitors. The lysates were incubated at 4° C. for 2 h with a 1:200 dilution of antibodies. Thirty microliters of protein A/G PLUS-agarose (sc-2003, Santa Cruz Biotechnology) were added and incubated at 4° C. for 1 h with rotation. The immune complexes were released from the beads by boiling in SDS-PAGE sample buffer for 5 min. Following electrophoresis on 10% SDS-PAGE gels, the immunoprecipitates were analyzed by western blotting with anti-Nucleolin.

8. Plasmids

Full-length mouse Cpne7 (mCpne7, NM_170684) cDNA, siRNA targeting Cpne7, and pGL3-Dspp vectors were constructed and verified as described previously (Thesleff I & Sharpe P (1997) Signaling networks regulating dental development. Mechanisms of development 67(2):111-123). Expression vectors encoding full-length human CPNE7, green fluorescent protein (GFP)-CPNE7 (NM_153636), and DDK (Flag)-tagged CPNE7 (NM_153636) were purchased from Origene (Rockville, Md.). Recombinant CPNE7 (NP 705900) was purchased from Origene. Control siRNA (sc-37007) and siRNA targeting nucleolin (sc-29230) were purchased from Santa Cruz Biotechnology (Santa Cruz, Calif.).

9. Reverse Transcription-polymerase Chain Reaction (RT-PCR) and Real-time PCR Analysis Total RNA was extracted from the cells with TRIzol® reagent (Invitrogen) according to the manufacturer's instructions. Total RNA (3 µg) was reverse transcribed using Superscript III reverse transcriptase (Invitrogen) and oligo (dT) primers (New England Biolabs, Ipswich, Mass.). One microliter of the RT product was amplified by PCR using the following primer pairs: Odam (462 bp, forward [F] 5'-atgtcctatgtggttcctgt-3' SEQ ID NO:3, reverse [R] 5'-ttatggttctcttaggctatc-3' SEQ ID NO:4), Cpne7 (178 bp, [F] 5'-cccgacccattgaccaagtc-3' SEQ ID NO:5, [R] 5'-catacacctcaaaccgtagcttc-3' SEQ ID NO:6), Mmp-20 (458 bp, [F] 5'-agctgtgagcaactgatgactgga-3' SEQ ID NO:7, [R] 5'-acagctagagccaagaacacacct-3' SEQ ID NO:8), Gapdh (452 bp, [F] 5'-accacagtccatgccatcac-3' SEQ ID NO:9, [R] 5'-tccaccaccctgttgctgt 3' SEQ ID NO:10), Dspp (141 bp, [F] 5'-gtgaggacaaggacgaatctga-3' SEQ ID NO:11, [R] 5'-cactactgtcactgctgtcact-3' SEQ ID NO:12), and Osteocalcin (283 bp, [F] 5'-ccacagccttcatgtccaag-3' SEQ ID NO:13, [R] 5'-ggcagagagagaggacaggg-3' SEQ ID NO:14). PCR was carried out under conditions of 30 cycles of 94° C. for 30 s, 55° C. for 30 s, and 72° C. for 1 min. The PCR products were electrophoresed in a 1% agarose gel, stained with ethidium bromide, and visualized under ultra violet light.

Real-time PCR was performed on an Applied Biosystems® 7500 sequence detection system (Applied Biosystems, Carlsbad, Calif.) using SYBR® Green PCR Master Mix according to the manufacturer's instructions. PCR conditions were 40 cycles of 95° C. for 1 min, 94° C. for 15 s, and 60° C. for 34 s. All reactions were run in triplicate, and PCR product levels were normalized to that of the housekeeping gene Gapdh. Relative changes in gene expression were calculated using the comparative threshold cycle (CT) method.

10. Preparation of Cytoplasmic and Nuclear Protein Extracts

The cells were collected by centrifugation at 3000 rpm for 5 min at 4° C. Cell lysis was performed in ice-cold hypotonic lysis buffer (10 mM HEPES, pH 7.9, 10 mM KCl, 0.1% Nonidet P-40 [NP-40]), supplemented with protease inhibitors (Roche Molecular Biochemicals, Mannheim, Germany) for 15 min. The nuclear and cytoplasmic fractions were separated by centrifugation at 3000 rpm for 5 min at 4° C. The resulting supernatant (cytoplasmic fraction) was stored at 4° C. until further analysis. The membrane pellet was resuspended in ice-cold hypertonic lysis buffer (10 mM HEPES, pH 7.9, 150 mM NaCl, 1% NP-40, 0.25% sodium deoxycholate, 10% glycerol) supplemented with protease inhibitors and incubated for 15 min at 4° C. The resulting supernatant (nuclear fraction) was stored at 4° C. until further analysis.

11. Preparation of CM and Inactivation of Cpne7

CM was harvested as described previously (1). Briefly, ALC cells were seeded at $7.5 \times 10^5$ cells/100-mm dish. When the cells reached 80% confluence, medium was replaced with differentiation medium. After 3 days of differentiation, the cells were washed twice with phosphate buffered saline (PBS) and incubated in differentiation medium without FBS for 24 h. The serum-free conditioned medium was harvested and concentrated to 1 µg/µl by ammonium sulfate precipitation. To inactivate Cpne7 in CM, 20 or 40 µg/ml anti-Cpne7 antibodies was mixed with CM for 2 h at 4° C. with rotation.

12. Transient Transfection and Luciferase Assay

HEK293 or MDPC-23 cells were seeded in 12-well culture plates at a density of $1.5 \times 10^5$ cells per well. The cells were transiently transfected using Metafectene® Pro reagent (Biontex, Martinsried/Planegg, Germany) with the constructs as described above. Construct pGL3-Dspp was cotransfected into MDPC-23 cells with the Cpne7 expression vector or the Cpne7 or Nucleolin siRNA vector. Following the addition of 50 µl luciferin to 50 µl of the cell lysate, luciferase activity was determined using an analytical luminescence luminometer (Promega, Madison, Wis.) according to the manufacturer's instructions.

13. DAPA (DNA Affinity Protein-binding Assay)

The binding assay was performed by mixing 600 µg of nuclear extract protein, 6 µg of biotinylated specific wild-type and mutated AP-1 site oligonucleotides spanning the Dspp promoter region-199 and -307 (SEQ ID NO: 15, 16, 17 and 18, respectively), and 60 µl of streptavidin-agarose beads. The mixture was incubated at 4° C. for 2 h with rotation. Beads were pelleted and washed three times with PBS. Bound proteins were eluted with loading buffer, separated by SDS-PAGE, and analyzed by western blotting.

14. Alizarin Red S Staining

MDPC-23 cells were fixed with 4% paraformaldehyde in PBS for 20 min. The cells were stained with a 1% alizarin red S (Sigma-Aldrich) solution in 0.1% $NH_4OH$ (pH 4.2) for 20 min at room temperature.

15. Animals, Tissue Preparation, and Immunohistochemistry

All experiments using animals followed protocols approved by the Institutional Animal Care and Use Committee of Seoul National University (SNU-111013-2). The heads of mice at embryonic day 19 (E19), postnatal day 7 (P7) and day 10 (P10) were decalcified in 10% EDTA (pH 7.4), embedded in paraffin, and processed for immunohistochemistry. Cpne7 expression was detected using an ABC kit (Vector Labs, Burlingame, Calif.) with rabbit anti-Cpne7 as the primary antibody and a biotin labeled goat anti-rabbit IgG (1:200, Vector Labs) as the secondary antibody.

16. Primary Cell Culture, In Vivo Transplantation, and Histological Analysis We collected human impacted third molars at Seoul National University Dental Hospital (Seoul, Korea). The experimental protocol was approved by the Institutional Review Board. Informed consent was obtained from the patients. Human DPCs were isolated and used in an in vivo transplantation experiment as described previously (1). The hDPCs ($2 \times 10^6$) were mixed with 100 mg hydroxyapatite/tricalcium phosphate (HA/TCP) ceramic powder (Zimmer, Warsaw, Ind.) alone, or with CM (30 µg), or with Cpne7 antibody-treated CM, or with rCpne7 (5 µg) in an 0.5% fibrin gel, and then transplanted subcutaneously into immune-compromised mice (NIH-bg-nu-xid; Harlan Laboratories, Indianapolis, Ind.) for 6 weeks. To inactivate Cpne7 in CM, Cpne7 antibody (5 µl) was mixed with CM for 24 h at 4° C. with rotation before in vivo transplantation in the Cpne7 antibody treated CM group. For histomorphometric analysis of newly formed mineralized tissue, hDPCs transfected with the Cpne7 overexpression or inactivation constructs were transplanted with HA/TCP particles for 12 weeks, as described above. To evaluate dentin/pulp-like tissue formation in root canal spaces, hDPCs ($2 \times 10^6$) were mixed with CM (10 µg) or Cpne7 antibody-treated CM in a 0.5% fibringel, and inserted into the empty root canal spaces of the human tooth segments for 12 weeks. Human-tooth segments were fabricated according to the protocol described in our previous study (Choung et al. (2013) The role of preameloblast-conditioned medium in dental pulp regeneration. J Mol Hist. 44:715-721). In addition, hBMSCs were also inserted into the empty root canal spaces with rCpne7 (5 µg) or rBmp2 (5 µg; Cowellmedi, Busan, Korea) for 6 weeks.

Samples were harvested and fixed in 4% paraformaldehyde, decalcified in 10% EDTA (pH 7.4), embedded in paraffin, and stained with hematoxylin-eosin (H-E) (Vector Labs) or processed for immunohistochemistry. For immunohistochemistry, proteins were detected with anti-DSP, anti-BSP (1), or anti-NESTIN (MAB353, Millipore) at a dilution of 1:100 as the primary antibody and a biotin labeled goat anti-rabbit IgG (Vector Labs) as the secondary antibody. The total area of generated mineralized tissue was analyzed using the LS starter program (Olympus Soft Imaging Solutions, Munster, Germany).

17. IPC (Indirect Capping) Model with Canine Teeth

Three beagle dogs (aged 2 year) were used for this experiment. Cervical parts of the maxillary and mandibular premolars were cleaned with 0.5% chlorhexidine. Then, dish-shaped class V cavities were prepared using a round bur (head diameter, 1 mm) with several gentle strokes, which prevent the exposure of the underlying pulp. The drilling was stopped when the color of the remaining dentin looked reddish gray. Teeth with exposed pulp were not used for the experiment. After sufficient irrigation, surgical sites were gently dried with a cotton pellet. The cavities were divided into 4 groups for the experiment. Group 1 received GI cement (GC Fuji II LC; GC America Inc.) only (control group), group 2 received GI cement after MTA (ProRoot MTA; Dentsply Tulsa Dental) treatment (MTA group), group 3 received GI cement after the topical treatment with the rCPNE7 protein (CPNE7 group), and group 4 received GI cement after the topical treatment with the rCPNE7 protein under MTA (CPNE7+MTA group). In groups 3 and 4, the topical application of rCPNE7 protein (total 1 µg of rCPNE7 per tooth in a buffer containing 25 mM Tris-HCl, 100 mM glycine, and 10% glycerol) were repeated and the samples were left for diffusion. Each group had 2 premolars per animal, totaling 24 premolars. Teeth with exposed pulp or remaining dentin thickness greater than 500 μm were not used for the experimental analysis.

18. Statistical Analyses

Statistical analyses were carried out using a Student's t-test. All statistical analyses were performed using SPSS software ver. 19.0

Results

Figure 3A:
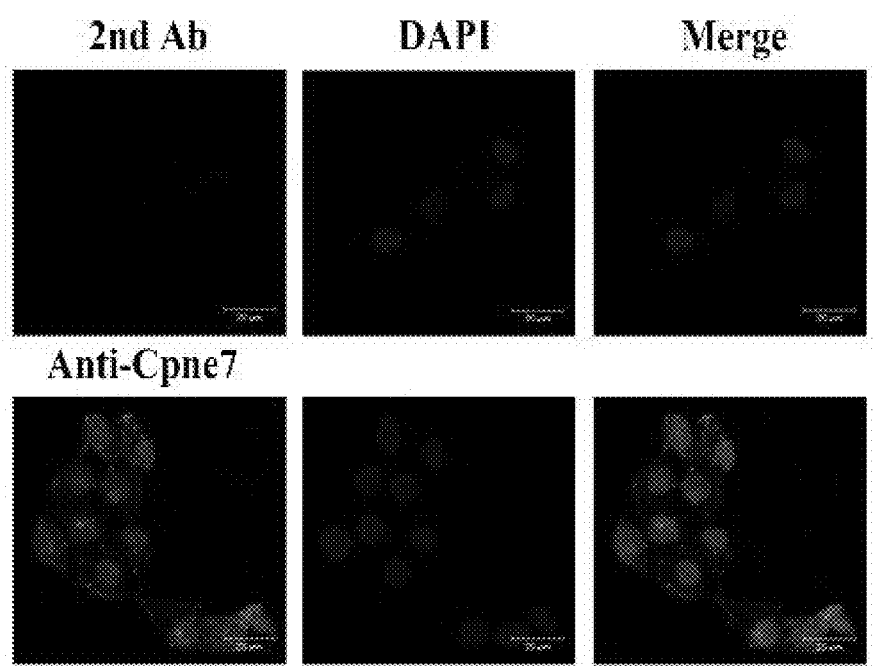
Figure 3B:
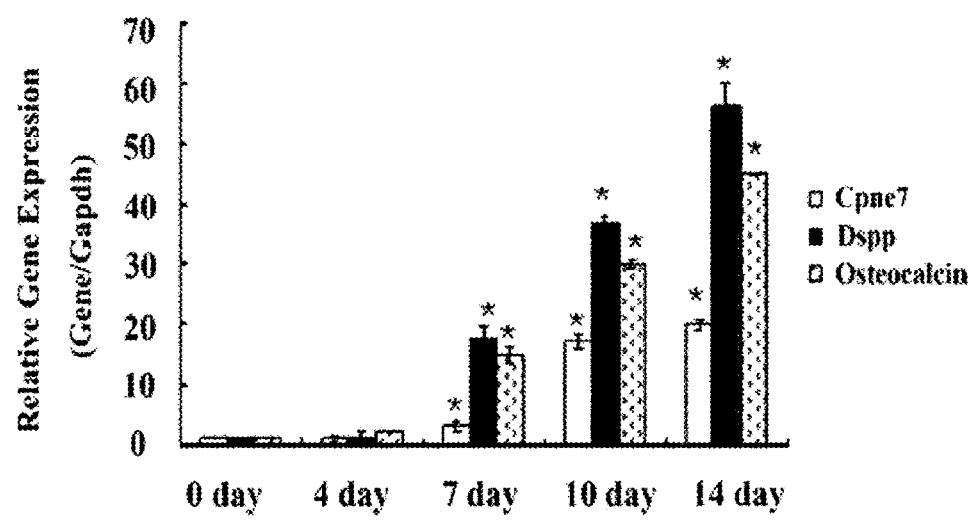

1. CPNE7 in Differentiating Odontoblasts Regulates Their Differentiation into Mature Odontoblasts In Vitro A spontaneously immortalized and cloned cell line MDPC-23 derived from dental papilla of 18-19 fetal day CD-1 mouse, which already induced by underlying inner enamel epithelium (Hanks C T, et al. (1998) Connective tissue research 37(3-4):233-249) were used in this study. To clarifying the functional role of translocated Cpne7 in differentiating odontoblasts, the expression pattern of endogenous odontoblast Cpne7 was evaluated in odontoblastic MDPC-23 cells. Cpne7 was localized mainly in nuclei of MDPC-23 cells (FIG. 3A). The expression levels of Cpne7 protein in differentiating odontoblasts increased from days 0 to 7 (early to middle stage of odontoblast differentiation), and then decreased from days 10 to 14 (late stage of odontoblast differentiation and mineralization). The expression of odontoblast differentiation markers, including Dsp and Osteocalcin, increased in odontoblasts from days 7 to 14, which was later than the increase in Cpne7 (FIGS. 3B and C). These findings provide significant evidences that nuclear Cpne7 in odontoblasts have functional roles in odontoblast differentiation, especially in early to middle stages.

Figure 4A:
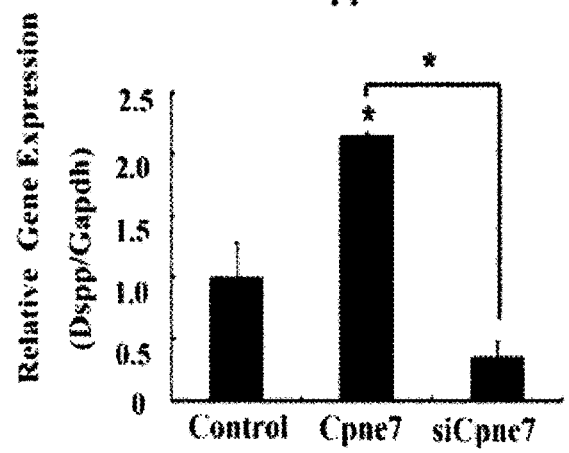
FIGS. 4A to 4G represent the control of odontoblast differentiation by CPNE7 stimulation and inactivation. MDPC-23 cells were transfected with CPNE7 expression construct alone for overexpression thereof or together with siRNA.
Figure 4B:
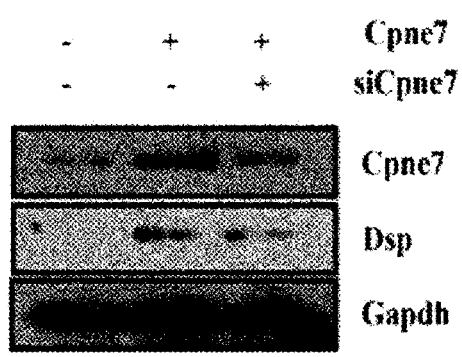
Figure 4C:
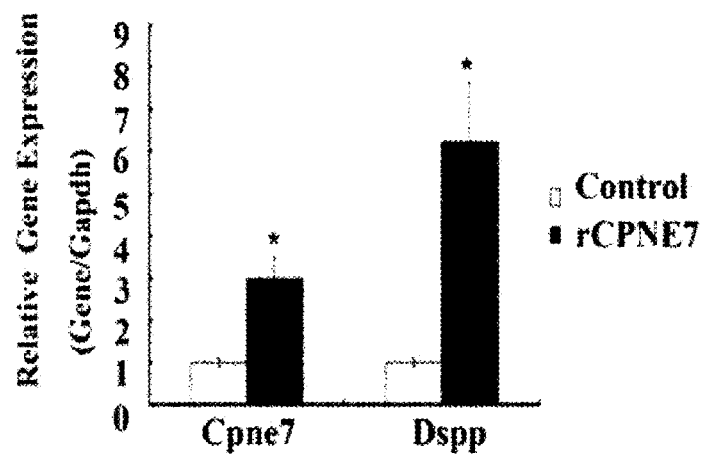
Figure 4D:
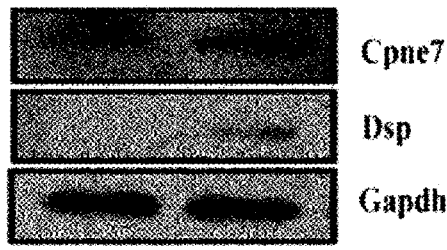
Figure 12:
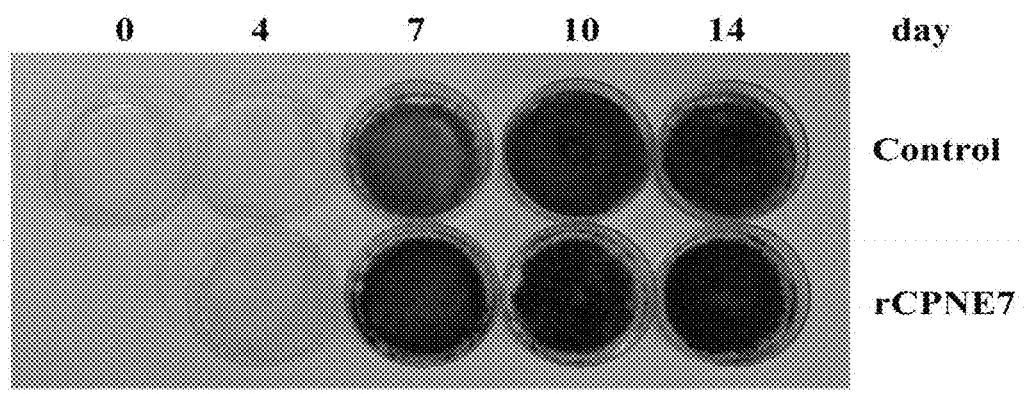
FIG. 12 shows the effects of rCPNE7 on mineralized nodule formation in vitro, in which MDPC-23 cells were cultured for 2 weeks with or without rCPNE7 treatment. The effect of rCPNE7 on mineralized nodule formation was analyzed by alizarin red S staining on the indicated days.

To investigate whether Cpne7 influences odontoblast differentiation by upregulating Dspp, we measured the expression levels of Dspp mRNA and Dsp protein after transfection of MDPC-23 cells with constructs encoding Cpne7 and Cpne7 siRNA. The expression level of Cpne7 was increased by transfection with Cpne7-encoding construct and effectively inhibited by Cpne7 siRNA in MDPC-23 and HEK293 cells, compared with control and cells transfected with control siRNA (FIGS. 11 and 4B). Cpne7 overexpression significantly increased the expression levels of Dspp mRNA and Dspp protein, whereas siRNA-mediated Cpne7 knockdown down regulated them in MDPC-23 cells (FIGS. 4A and B). To confirm whether exogenous Cpne7 also enhanced Dspp expression, we investigated the effects of recombinant CPNE7 (rCPNE7) on Dspp expression in MDPC-23 cells. As expected, rCPNE7 treatment also increased the expression levels of Dspp mRNA and Dsp protein in MDPC-23 cells (FIGS. 4C and D). Recombinant Cpne7 treatment enhanced mineralized nodule formation compared to control during odontoblast differentiation in vitro (FIG. 12). These data suggest that Cpne7 regulate Dspp expression and control odontoblast differentiation and mineralization.

Figure 4E:
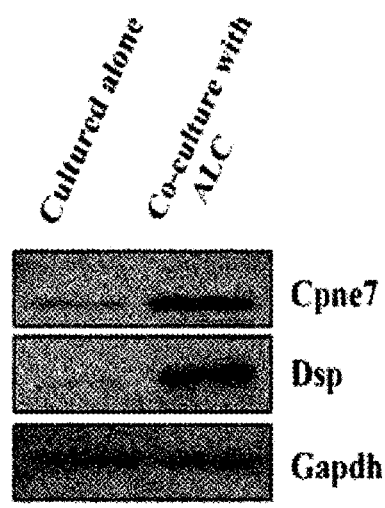
Figure 4F:
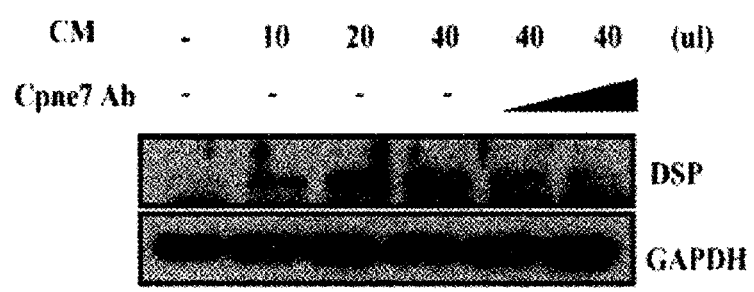
Figure 4G:
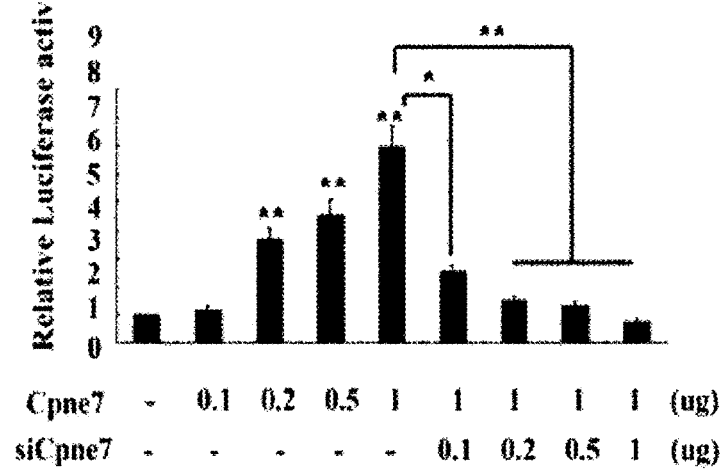

Next approach was taken to confirm the functional consequences of Cpne7 and Dspp gene expression. Similar to our previous results (6), co-culture with ALCs enhanced the expression levels of Cpne7 and Dsp protein in MDPC-23 cells (FIG. 4E). The Dsp protein was increased in a dose dependent manner by treatment with PA-CM, but decreased by treatment with increasing concentrations of Cpne7-specific antibody for inactivation (FIG. 4F). Moreover, the Dspp transcriptional activity was significantly promoted by overexpression of Cpne7, but suppressed by siRNA-mediated Cpne7 knockdown (FIG. 4G). Collectively, these results indicate that Cpne7 regulates odontoblast differentiation and mineralization via control of Dspp expression In sum, the above results indicate that CPNE7 regulates the differentiation into odontoblast and mineralization via regulating the expression of Dspp.

Figure 5:
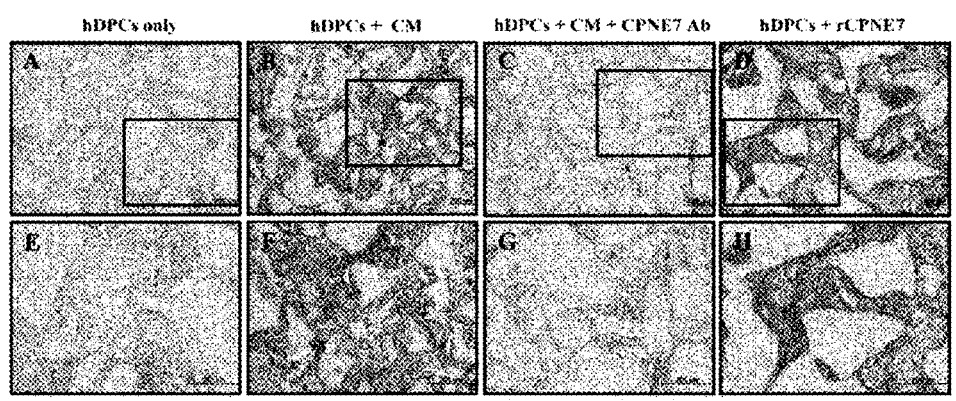
FIG. 5 shows the histological analysis results of the complex of dentin/pulp tissue generated using hDPCs (human dental pulp tissue cells) in vivo., in which hDPCs was subcutaneously transplanted to immune compromised mice with 100 mg HA/TCP (A and E), or CM (B and F), CPNE7 antibody treated CM (C and G), or rCPNE7 (D and H) mixed with 0.5% fibrin gel. After 6 weeks, the samples were obtained from the mice and stained with H&E (E-H). The boxed areas in A-D were enlarged. Scale bar: 200 μm.

2. Cpne7 Induces the Differentiation of Dental Mesenchymal Stem Cells, Such as Human Dental Pulp Cells (hDPCs), into Odontoblasts and Dentin Formation In Vivo To determine the role of Cpne7 in odontoblast differentiation and dentin formation in vivo, we transplanted hDPCs into the subcutaneous tissues of immunocompromised mice in the presence of hydroxyapatite/tricalcium phosphate (HA/TCP) under four different conditions, hDPCs only, hDPCs with PA-CM, hDPCs with PA-CM and Cpne7 antibody, and hDPCs with rCPNE7. Six weeks after transplantation, dentin/pulp-like tissues were formed at the periphery of HA/TCP particles in all groups (FIG. 5A-H). PA-CM- or rCPNE7-treated groups exhibited dentin/pulp complex characteristics with odontoblasts more typical than the hDPCs-only group (FIGS. 5E, F, and H). However, in the group treated with Cpne7 antibody-treated PA-CM for inactivation, mineralized tissue formation was barely observed (FIGS. 5F and G).

Based on the results of in vitro experiments shown in FIG. 4, we transplanted hDPCs transfected with Cpne7-encoding, Cpne7 siRNA, or control siRNA constructs into subcutaneous tissue in order to evaluate the effects of the Cpne7 gene on dentin/pulp-like tissue formation in vivo. Twelve weeks after transplantation, hDPCs-only, Cpne7 overexpression, and control siRNA groups showed the generation of dentin-like mineralized tissues at the periphery of HA/TCP particles, whereas the Cpne7 siRNA group revealed little evidence of mineralization (FIG. 6A-H). According to the histomorphometric analysis of each group, overexpression of Cpne7 in hDPCs was associated with the highest level of dentin-like mineralized tissue formation in vivo and siRNA-mediated knockdown of Cpne7 was associated with the least. There was no significant difference between the hDPCs-only and control siRNA groups (FIG. 6I).

Figure 7:
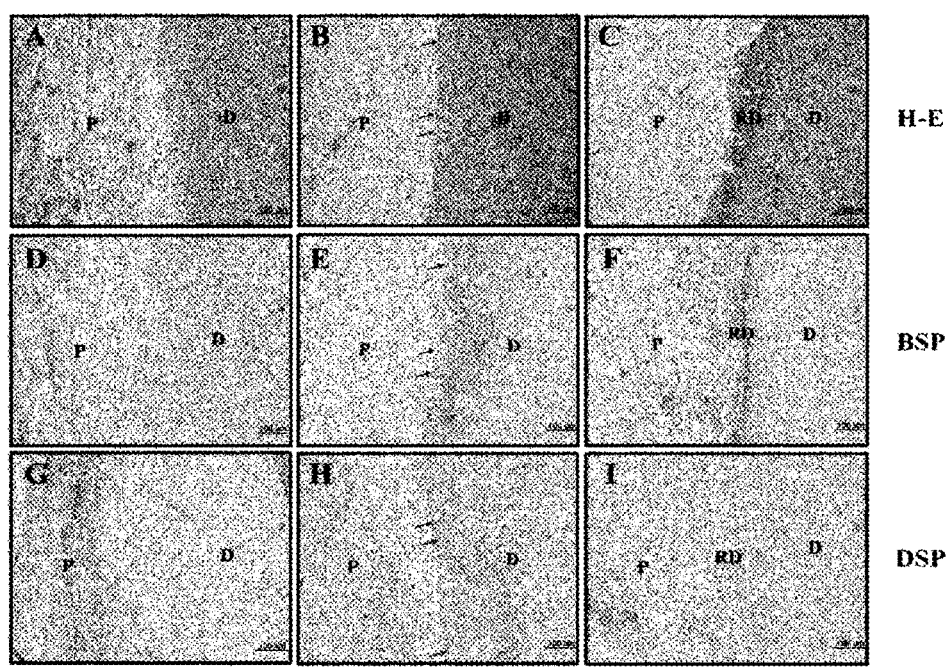
FIG. 7 shows the results of dentin/pulp-like tissue formation in root canal space of human teeth at 12 weeks after the transplantation, in which hDPCs alone (A, D, G) or together with CM (B, E, H) or CPNE7 antibody treated CM (C, F, I) in 0.5% fibrin gel were injected into a root canal space. After 12 weeks, the regenerated tissues were stained with H&E (A-C), or immune-stained with anti-BSP (D-F) or anti-DSP (G-I). The Arrows in B, E, and H indicate the regenerated odontoblast with odontoblastic processes. P: regenerated pulp, D: pre-existing dentin wall, RD: newly formed reparative dentin. Scale bars, 100 µm.

The tooth segments, which consist of natural dentinal wall and empty pulp cavity, provide the specific local environment for the regeneration of dentin/pulp-like tissues by dental stem cells (Huang G T, et al. (2010) Tissue engineering. Part A 16(2):605-615). To evaluate dentin/pulp-like tissue formation in root canal spaces, hDPCs were mixed with or without PA-CM or Cpne7 antibody-treated PA-CM, and transplanted into subcutaneous tissue of immune-compromised mice. After twelve weeks of implantation, vascularized pulp-like tissue regenerated inside the root canal spaces in all groups (FIG. 7A-C). In the PA-CM-treated group, odontoblast-like cells exhibited a palisade arrangement on the existing dentinal wall, and their cytoplasmic processes, with lengthened nuclei, extended toward existing dentinal tubules (FIGS. 7B, E, and H). In the Cpne7 antibody-treated PA-CM group, however, reparative dentin-like mineralized tissues showing entrapped cells was observed between newly formed pulp-like tissue and the existing dentin. BSP was distinctly expressed in the newly-formed reparative dentin area of the Cpne7 antibody-treated PA-CM group compared to hDPCs-only and PA-CM-treated group (FIG. 7D-F). However, DSP was clearly detected in the PA-CM group, but only faint staining was observed in the Cpne7 antibody-treated CM group (FIG. 7G-I).

Taken together, these in vivo findings indicate that, among preameloblast-derived factors, Cpne7 plays an important functional role in regeneration of the dentin/pulp complex and induces the odontogenic differentiation of mesenchymal stem cells of dental origin, such as hDPCs.

3. Cpne7 Induces Differentiation of Mesenchymal Stem Cells of Non-dental Origin into Odontoblasts In Vivo and In Vitro In the present Example, the role of Cpne7 in the differentiation of mesenchymal stem cell of non-dental origin was examined. Non-dental origin cells were shown previously not induced by dental epithelium. Here C3H10T1/2 cells, which are established from mouse embryonic connective tissue and do not differentiate into odontoblast-like cells, and human bone marrow mesenchymal stem cells (hBMSCs) were used.

First, the effects of ALC (Ameloblast like cells) co-culture or Cpne7 overexpression in C3H10T1/2 cells were examined. As a result, Cpne7 was not expressed in both control C3H10T1/2 cells and those cells cultured for 5 days in differentiation medium. However, C3H10T1/2 cells co-cultured with ALCs showed Cpne7 expression by western blotting, although the expression levels were low. The ameloblastic ALCs also induced Dmp1 and Dspp expression in C3H10T1/2 cells (FIG. 8A). In addition, Cpne7 overexpression clearly induced Dspp protein expression in C3H10T1/2 cells (FIG. 8B).

Next, further in vivo experiments using hBMSCs with or without rCPNE7 or rBMP2 proteins in empty root canal spaces for 6 weeks were performed. In the rCPNE7-treated hBMSCs group, these non-dental mesenchymal stem cells differentiated into odontoblast-like cells with odontoblastic cellular processes and dentin-like mineralized tissues, including regeneration of the structure of dentinal tubules on the existing dentinal wall (FIG. 8C-E). The cellular processes of odontoblast-like cells extended toward the dentinal tubules of newly formed dentin-like tissues, which robustly expressed DSP and NESTIN (FIG. 8F-K). On the other hand, no obvious dentin-like structures or DSP or NESTIN expression were observed in hBMSCs-only and rBMP2-treated hBMSCs groups.

Taken together, these findings suggest that Cpne7 from preameloblasts might act as a signaling molecule in the odontogenic induction process and, thus, be capable of programming mesenchymal stem cells of non-dental origin, as well as those of dental origin, into odontoblast-like cells in vivo and in vitro.

4. Identification of Mechanism Underlying the Differentiation into Odontoblast Like Cells by Cpne7.

Our data showed that Cpne7 regulated Dspp gene expression in odontoblastic MDPC-23 cells. However, there is no DNA-binding motif in the structure of copine family members (Creutz C E, et al. (1998) The Journal of biological chemistry 273(3):1393-1402; Tomsig J L, Sohma H, & Creutz C E (2004) The Biochemical journal 378(Pt 3):1089-1094). Therefore, we further investigated other potential effectors of Cpne7-mediated Dspp expression because copine family proteins contain two distinctive domains, a phospholipid-binding domain and a protein interaction domain. Nucleolin is a multifunctional protein that is involved in many cellular activities, including cell proliferation, embryogenesis, and cell death. Nucleolin plays a functional role in tooth development and interacts with Cpne7.

To provide further evidence for an interaction between Cpne7 and Nucleolin, we performed immunocytochemical and co-immunoprecipitation (co-IP) analyses of MDPC-23 cells. Notably, both endogenous and exogenous Cpne7 proteins showed strong co-localization with Nucleolin protein in nuclei of odontoblasts (FIG. 9A) and interacted with Nucleolin (FIG. 9B). Next, we investigated whether the Cpne7-Nucleolin complex binds specifically to the Dspp promoter. A positive control was designed using the well-characterized nuclear factor I-C antibody on DSPP promoter. Chromatin immunoprecipitation (ChIP) assay revealed that Nucleolin bound to the Dspp promoter, whereas negative control (pre-immune serum) or Nucleolin siRNA did not precipitate the Dspp promoter fragment (FIG. 9C, middle). Also, Cpne7 remained bound to the Dspp promoter (FIG. 9C, lower). To confirm that Nucleolin is sufficient to interact with the AP-1 site of the Dspp promoter, we used a DNA affinity protein-binding assay (DAPA) with biotin-labeled AP-1 site. Nucleolin was associated with the wild-type AP-1 site, but not with the mutated sequence (FIG. 13).

Figure 9D:
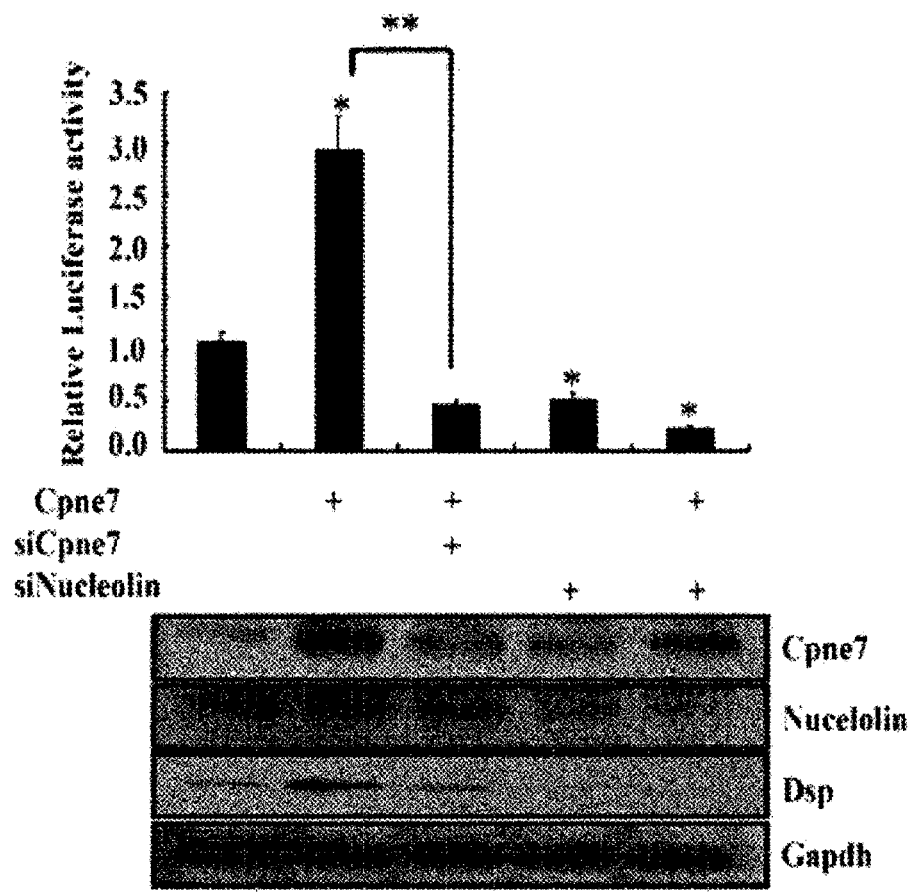

Finally, to further investigate the effect of Nucleolin on Cpne7-mediated Dspp transcription, we transfected MDPC-23 cells with Nucleolin siRNA constructs and conducted luciferase reporter assays using a Dspp-responsive reporter. In these cells, Nucleolin level was reduced by Nucleolin siRNA, without alteration of Cpne7 level (FIG. 9D, lower). Cpne7 stimulated Dspp promoter activity and this activation was abolished with the knockdown of Nucleolin (FIG. 9D, upper). These data indicated that Nucleolin is critical for Cpne7-dependent Dspp transcription. Taken together, the results suggest that Cpne7 as a coregulator is physically associated with Nucleolin protein, and the Cpne7-Nucleolin complex modulates Dspp gene transcription 5. The Formation of Physiologic Reactionary Dentin in IPC (Indirect Pulp Capping) by CPNE7 Alone or in Combination with MTA in Canine Model.

Figure 14:
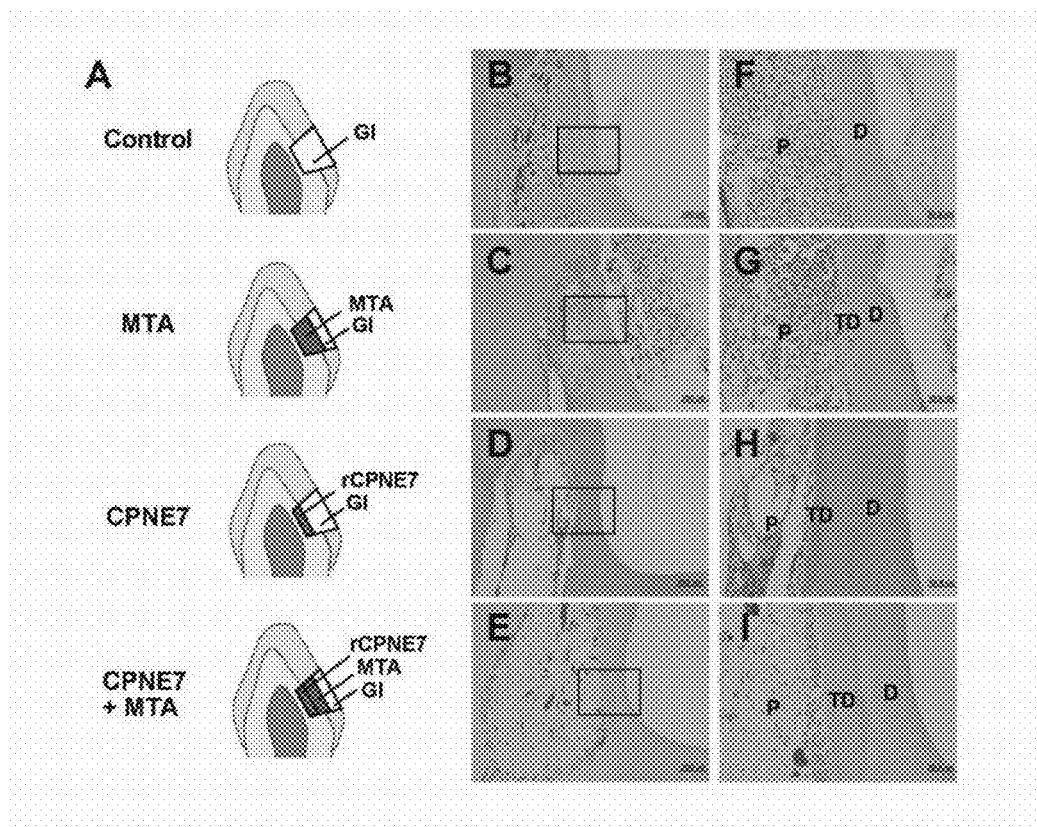
FIG. 14 shows a result of Indirect pulp capping (IPC) in canine model: (A) Schematic diagrams of the IPC model. Defect areas were covered with glass ionomer (GI) cement only (control group), GI cement after mineral trioxide aggregate (MTA) sealing (MTA group), GI cement after the topical treatment with recombinant copine7 (CPNE7 group), and GI cement after the topical treatment with recombinant copine7 (rCPNE7) under MTA sealing (CPNE7+MTA group). (B-M) Histological analysis of dental pulp responses at the IPC area after 3 wks by hematoxylin/eosin staining (4 of 6 samples from each group). (B, F, and J) Control group. (C, G, and K) MTA group. (D, H, and L) CPNE7 group. (E, I, and M) CPNE7+MTA group. (F-I) Boxed areas in B-E are shown at higher magnification in F-I. (J-M) Boxed areas in F-I are shown at higher magnification in J-M. Arrows in K indicate the cellular components in the calcified matrix. Scale bars, 200 µm (B-E), 50 µm (F-I), and 20 µm (J-M). D, remaining dentin; P, pulp, TD, newly formed tertiary dentin.

The possibility or potential of CPNE7 as a pulp capping material alone or together with MTA was tested. Prepared cavities were divided into 4 groups (FIG. 14, A): GI cement only (control group), GI cement after MTA sealing (MTA group), GI cement after topical treatment of rCPNE7 (CPNE7 group), and GI cement after topical treatment for CPNE7 under MTA sealing (CPNE7+MTA group). In the control group, newly formed mineralized tissue was rarely detected in the pulp cavity (FIGS. 3B, F, and J), whereas in the MTA group, irregular features of tertiary dentin were generated beneath the remaining dentin at cavity-prepared sites (FIGS. 14, C, G and K). This newly generated dentin was considered reparative dentin, which has a tubular structures with cellular components in the calcified matrix (arrows in FIG. 3K). In the CPNE7 group, the regeneration of physiologic tertiary dentin was clearly observed beneath the remaining dentin at cavity-prepared sites (FIGS. 14, D, H, and L). The regenerated dentin showed typical characteristics of reactionary dentin, such as odontoblast processes, and was continuous with remaining original dentin structures. Tertiary dentin was also regenerated in the CPNE7+MTA group and showed typical reactionary dentinal structures as in the CPNE7 group (FIGS. 14, E, I, and M). Unlike the MTA group, characteristics of reparative dentin were hardly detected. The overall thickness of the regenerated tertiary dentin in the CPNE7+MTA group was thicker than in the CPNE7 group. Furthermore, odontoblasts formed a typical layer beneath the regenerated dentin.

Therefore, this result indicates that CPNE7 protein alone or in combination with MTA can be used advantageously as an indirect pulp capping material by generating reactionary dentin which is identical to the physiologic tertiary dentin, in comparison to MTA which produces reparative dentin, which is similar to bone. Further it indicates that the use of CPNE7 together with MTA can complement the disadvantage of MTA producing reparative dentin as well as increases the formation of physiological reactionary dentin.

6. The Effect of CPNE7 for Treating Dentin Hypersensitivity Alone or in Combination with MTA In FIG. 15, the morphological features of pulp-side surfaces of the remaining original dentin and dentinal tubules were examined by scanning electron microscopy (SEM) was performed at the original dentin/pulp (control group) or original dentin/tertiary dentin (MTA, CPNE7, and CPNE7+ MTA groups) interfaces of cavity prepared sites via the gap of the tertiary dentin matrix after removal of the dental pulp tissues (FIG. 15, A-E). A large portion of the dentinal tubules of the original dentin was occluded with mineral deposition of peritubular dentin in the CPNE7 and CPNE7+MTA groups, whereas those in the control group were open and no precipitate was observed (FIGS. 15, F, H, and I). In the MTA group, some of the dentinal tubules were slightly occluded, although most of the dentinal tubules remained open (FIG. 15, G). As a result, it was confirmed that a so-called peritubular dentin in which most of the dental tubules were observed to clog was formed in the group treated with CPNE7 protein alone and in the group treated with CPNE7 protein in combination with MTA, in comparison with the control group and the group treated with MTA only. This study confirms the possibility of using CPNE7 protein (alone or in combination with MTA) as a pharmaceutical composition for clinical treatment of dentin hypersensitivity or to treat dentin hypersensitivity.

Dentin hypersensitivity is a common dental disease characterized by pain derived from exposed dentin in response to thermal, chemical, or osmotic stimuli. In general, 2 types of clinical treatments have been suggested to relieve such pain, including occlusion of dentinal tubules and interruption of the transmission of nerve impulses (Dababneh et al. (1999) Dentine hypersensitivity—an enigma? A review of terminology, mechanisms, aetiology and management. British dental journal. 187(11):606-611; discussion 603). To occlude dentinal tubules, fluorides, varnishes, adhesive resins, lasers, or restorative materials have been used for treatment; however, these are neither sufficient nor very successful (Davari et al. (2013) Dentin hypersensitivity: Etiology, diagnosis and treatment; a literature review. J Dent (Shiraz.) 14(3):136-145). In the current study, CPNE7 or CPNE7 under an MTA sealing treatment of the exposed canine dentin showed that dentinal tubules of the remaining dentin were almost occluded as observed under SEM. This result suggests that CPNE7 stimulates odontoblasts to produce intratubular dentin, as well as reactionary dentin, for the reduction of dentin permeability and protection against painful stimuli through dentinal tubules.

While one or more exemplary embodiments have been described with reference to the figures, it will be understood by those of ordinary skill in the art that various changes in form and details may be made therein without departing from the spirit and scope of the inventive concept as defined by the following claims.

Unless otherwise defined, all the terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

What is claimed is:

1. A method of treating dentin hypersensitivity comprising:
administering to a subject in need thereof an effective amount of (i) an isolated CPNE7 protein or a gene encoding the same; (ii) a cell overexpressing a CPNE7 protein; (iii) a mesenchymal stem cell overexpressing a CPNE7 protein; (iv) an odontoblast differentiated from the mesenchymal stem cell of (iii); or (v) the isolated CPNE7 protein or gene of (i) in combination with a mesenchymal stem cell, thereby treating the dentin hypersensitivity in the subject,
wherein the (i), (ii), (iii), (iv), or (v) further comprises MTA (Mineral Trioxide Aggregate) or calcium hydroxide (Ca(OH)$_2$).

2. The method of claim 1, wherein the cell overexpressing a CPNE7 protein is a mesenchymal stem cell.

3. The method of claim 2, wherein the mesenchymal stem cell is of non-dental origin.

4. A method of generating reactionary pulp in an affected area comprising:
treating the affected area with an effective amount of (i) an isolated CPNE7 protein or a gene encoding the same; (ii) a cell overexpressing a CPNE7 protein; (iii) a mesenchymal stem cell overexpressing a CPNE7 protein; (iv) an odontoblast differentiated from the mesenchymal stem cell of (iii); or (v) the isolated CPNE7protein or the gene of (i) in combination with a mesenchymal stem cell, thereby generating reactionary pulp in the affected area,
wherein the (i), (ii), (iii), (iv) or (v) further comprises MTA (Mineral Trioxide Aggregate) or calcium hydroxide (Ca(OH)$_2$.

5. The method of claim 4, wherein the cell overexpressing a CPNE7 protein is a mesenchymal stem cell.

6. The method of claim 5, wherein the mesenchymal stem cell is of non-dental origin.

7. A method of regenerating dentin or pulp in an affected area comprising:
treating the affected area with an effective amount of (i) an isolated CPNE7 protein or a gene encoding the same; (ii) a cell overexpressing a CPNE7 protein; (iii) a mesenchymal stem cell overexpressing a CPNE7 protein; (iv) an odontoblast differentiated from the mesenchymal stem cell of (iii); or (iv) the isolated CPNE7 protein or gene of (i) in combination with a mesenchymal stem cell, thereby regenerating the dentin or pulp in the affected area,
wherein the (i),(ii), (iii), (iv) or (v) further comprises MTA (Mineral Trioxide Aggregate) or calcium hydroxide (Ca(OH)$_2$).

8. The method of claim 7, wherein the cell overexpressing a CPNE7 protein is a mesenchymal stem cell.

9. The method of claim 8, wherein the mesenchymal stem cell is of non-dental origin.

10. A method of indirect pulp capping in an affected area comprising:
treating the affected area with an effective amount of (i) an isolated CPNE7 protein or gene encoding the same; (ii) a cell overexpressing a CPNE7 protein; (iii) a mesenchymal stem cell overexpressing a CPNE7 protein; (iv) an odontoblast differentiated from the mesenchymal stem cell of (iii); or (v) the isolated CPNE7 protein or the gene of (i) in combination with a mesenchymal stem cell, thereby performing indirect pulp capping in the affected area, wherein the (i), (ii), (iii), (iv) or (v) further comprises MTA (Mineral Trioxide Aggregate) or calcium hydroxide (Ca(OH)$_2$).

11. The method of claim 10, wherein the cell overexpressing a CPNE7 protein is a mesenchymal stem cell.

12. The method of claim 11, wherein the mesenchymal stem cell is of non-dental origin.

* * * * *

```
                        SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Forward primer for Dspp -400 region

<400> SEQUENCE: 1
gggtcttaaa tagccagtcg                                              20

<210> SEQ ID NO 2
<211> LENGTH: 18
<212> TYPE: DNA
<213> ORGANISM: Artificial Sequence
<220> FEATURE:
<223> OTHER INFORMATION: Reverse primer for Dspp -10 region

<400> SEQUENCE: 2
ctgagagtgg cacactgt                                                18

<210> SEQ ID NO 3
<211> LENGTH: 20
<212> TYPE: DNA
<213> ORGANISM: Artificial Sequence
<220> FEATURE:
<223> OTHER INFORMATION: Forward primer for Odam

<400> SEQUENCE: 3
atgtcctatg tggttcctgt                                              20
```

```
<210> SEQ ID NO 4
<211> LENGTH: 21
<212> TYPE: DNA
<213> ORGANISM: Artificial Sequence
<220> FEATURE:
<223> OTHER INFORMATION: Reverse primer for Odam

<400> SEQUENCE: 4
ttatggttct cttaggctat c                                              21

<210> SEQ ID NO 5
<211> LENGTH: 20
<212> TYPE: DNA
<213> ORGANISM: Artificial Sequence
<220> FEATURE:
<223> OTHER INFORMATION: Forward primer for Cpne7

<400> SEQUENCE: 5
cccgacccat tgaccaagtc                                                20

<210> SEQ ID NO 6
<211> LENGTH: 23
<212> TYPE: DNA
<213> ORGANISM: Artificial Sequence
<220> FEATURE:
<223> OTHER INFORMATION: Reverse primer for Cpne7

<400> SEQUENCE: 6
catacacctc aaaccgtagc ttc                                            23

<210> SEQ ID NO 7
<211> LENGTH: 24
<212> TYPE: DNA
<213> ORGANISM: Artificial Sequence
<220> FEATURE:
<223> OTHER INFORMATION: Forward primer for Mmp-20

<400> SEQUENCE: 7
agctgtgagc aactgatgac tgga                                           24

<210> SEQ ID NO 8
<211> LENGTH: 24
<212> TYPE: DNA
<213> ORGANISM: Artificial Sequence
<220> FEATURE:
<223> OTHER INFORMATION: Reverse primer for Mmp-20

<400> SEQUENCE: 8
acagctagag ccaagaacac acct                                           24

<210> SEQ ID NO 9
<211> LENGTH: 20
<212> TYPE: DNA
<213> ORGANISM: Artificial Sequence
<220> FEATURE:
<223> OTHER INFORMATION: Forward primer for Gapdh

<400> SEQUENCE: 9
accacagtcc atgccatcac                                                20

<210> SEQ ID NO 10
<211> LENGTH: 19
<212> TYPE: DNA
<213> ORGANISM: Artificial Sequence
<220> FEATURE:
<223> OTHER INFORMATION: Reverse primer for Gapdh
```

```
<400> SEQUENCE: 10
tccaccaccc tgttgctgt                                              19

<210> SEQ ID NO 11
<211> LENGTH: 22
<212> TYPE: DNA
<213> ORGANISM: Artificial Sequence
<220> FEATURE:
<223> OTHER INFORMATION: Forward primer for Dspp

<400> SEQUENCE: 11
gtgaggacaa ggacgaatct ga                                          22

<210> SEQ ID NO 12
<211> LENGTH: 22
<212> TYPE: DNA
<213> ORGANISM: Artificial Sequence
<220> FEATURE:
<223> OTHER INFORMATION: Reverse primer for Dspp

<400> SEQUENCE: 12
cactactgtc actgctgtca ct                                          22

<210> SEQ ID NO 13
<211> LENGTH: 20
<212> TYPE: DNA
<213> ORGANISM: Artificial Sequence
<220> FEATURE:
<223> OTHER INFORMATION: Forward primer for Osteocalcin

<400> SEQUENCE: 13
ccacagcctt catgtccaag                                             20

<210> SEQ ID NO 14
<211> LENGTH: 20
<212> TYPE: DNA
<213> ORGANISM: Artificial Sequence
<220> FEATURE:
<223> OTHER INFORMATION: Reverse primer for Osteocalcin

<400> SEQUENCE: 14
ggcagagaga gaggacaggg                                             20

<210> SEQ ID NO 15
<211> LENGTH: 25
<212> TYPE: DNA
<213> ORGANISM: Artificial Sequence
<220> FEATURE:
<223> OTHER INFORMATION: AP-1 binding site (-199) in DSPP promoter

<400> SEQUENCE: 15
ataggcacac tgactcttta aaccc                                       25

<210> SEQ ID NO 16
<211> LENGTH: 25
<212> TYPE: DNA
<213> ORGANISM: Artificial Sequence
<220> FEATURE:
<223> OTHER INFORMATION: AP-1 binding site (-199) mutant in DSPP
      promoter
<220> FEATURE:
<221> NAME/KEY: mutation
<222> LOCATION: (12)
<220> FEATURE:
<221> NAME/KEY: mutation
<222> LOCATION: (15)
```

-continued

```
<400> SEQUENCE: 16
ataggcacac ttacccttta aaccc                                              25

<210> SEQ ID NO 17
<211> LENGTH: 25
<212> TYPE: DNA
<213> ORGANISM: Artificial Sequence
<220> FEATURE:
<223> OTHER INFORMATION: AP-1 binding site (-307) in DSPP promoter

<400> SEQUENCE: 17
aatgcagggt gacagagtct aagtg                                              25

<210> SEQ ID NO 18
<211> LENGTH: 25
<212> TYPE: DNA
<213> ORGANISM: Artificial Sequence
<220> FEATURE:
<223> OTHER INFORMATION: AP-1 binding site (-307) in DSPP promoter with
      mutations
<220> FEATURE:
<221> NAME/KEY: mutation
<222> LOCATION: (12)
<220> FEATURE:
<221> NAME/KEY: mutation
<222> LOCATION: (14)

<400> SEQUENCE: 18
aatgcagggt gcccgagtct aagtg                                              25
```